US008314089B2

(12) United States Patent
Schohe-Loop et al.

(10) Patent No.: US 8,314,089 B2
(45) Date of Patent: Nov. 20, 2012

(54) SUBSTITUTED PYRAZOLAMIDES AND THEIR USE

(75) Inventors: Rudolf Schohe-Loop, Wuppertal (DE); Reinhold Welker, Bensheim (DE); Arnold Paessens, Haan (DE); Marcus Bauser, Berlin (DE); Friederike Stoll, Duesseldorf (DE); Frank Dittmer, Duesseldorf (DE); Kerstin Henninger, Wuppertal (DE); Daniela Paulsen, Wuppertal (DE); Dieter Lang, Velbert (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 12/884,113

(22) Filed: Sep. 16, 2010

(65) Prior Publication Data

US 2011/0172207 A1    Jul. 14, 2011

Related U.S. Application Data

(63) Continuation of application No. PCT/EP2009/001877, filed on Mar. 14, 2009.

(30) Foreign Application Priority Data

Mar. 17, 2008  (DE) .......................... 10 2008 015 032

(51) Int. Cl.
| A61K 31/4155 | (2006.01) |
| A61K 31/5377 | (2006.01) |
| A61K 31/5386 | (2006.01) |
| A61K 31/553 | (2006.01) |
| A61K 31/496 | (2006.01) |
| C07D 413/06 | (2006.01) |
| C07D 417/06 | (2006.01) |
| C07D 403/06 | (2006.01) |
| A61P 31/12 | (2006.01) |

(52) U.S. Cl. ............. 514/211.15; 514/227.8; 514/230.5; 514/254.05; 514/365; 514/406; 544/58.4; 544/105; 544/140; 544/371; 548/200; 548/364.1

(58) Field of Classification Search .................. None
See application file for complete search history.

(56) References Cited

U.S. PATENT DOCUMENTS

| 3,806,506 A | 4/1974 | Felauer et al. |
| 4,684,652 A | 8/1987 | Dubroeucq et al. |
| 5,134,142 A | 7/1992 | Matsuo et al. |
| 5,432,835 A | 7/1995 | Hashimoto |
| 5,571,810 A | 11/1996 | Matsuo et al. |
| 5,624,941 A | 4/1997 | Barth et al. |
| 5,627,203 A | 5/1997 | Rault et al. |
| 6,143,780 A | 11/2000 | Brouwer et al. |
| 7,622,471 B2 | 11/2009 | Kanaya et al. |
| 2004/0116425 A1 | 6/2004 | Li et al. |
| 2005/0054707 A1 | 3/2005 | Edwards et al. |
| 2008/0064682 A1 | 3/2008 | Kanaya et al. |

FOREIGN PATENT DOCUMENTS

| DE | 10 2004 054 | 5/2006 |
| EP | 0 065 295 | 11/1982 |
| EP | 0 112 776 | 7/1984 |
| EP | 0 418 845 | 3/1991 |
| EP | 0 554 829 | 8/1993 |
| EP | 0 576 357 | 12/1993 |
| EP | 1 591 443 | 11/2005 |
| EP | 1 743 637 | 1/2007 |
| EP | 1 762 568 | 3/2007 |
| WO | WO-91/19708 | 12/1991 |
| WO | WO-94/27979 | 12/1994 |
| WO | WO-97/19940 | 6/1997 |
| WO | WO-02/00649 | 1/2002 |
| WO | WO-02/100853 | 12/2002 |
| WO | WO-03/014107 | 2/2003 |
| WO | WO-03/037274 | 5/2003 |
| WO | WO-2004/016592 | 2/2004 |
| WO | WO-2004/024147 | 3/2004 |
| WO | WO-2004/031178 | 4/2004 |
| WO | WO-2004/050632 | 6/2004 |
| WO | WO-2004/076453 | 9/2004 |
| WO | WO-2005/000820 | 1/2005 |
| WO | WO-2005/002576 | 1/2005 |
| WO | WO-2005/007625 | 1/2005 |
| WO | WO-2005/035488 | 4/2005 |
| WO | WO-2005/080343 | 9/2005 |
| WO | WO-2006/015860 | 2/2006 |
| WO | WO-2006/023462 | 3/2006 |
| WO | WO-2006/062982 | 6/2006 |
| WO | WO-2006/062984 | 6/2006 |
| WO | WO-2006/065209 | 6/2006 |
| WO | WO-2006/099231 | 9/2006 |
| WO | WO-2007/002559 | 1/2007 |
| WO | WO-2007/009701 | 1/2007 |
| WO | WO-2007/020388 | 2/2007 |
| WO | WO-2008/043775 | 4/2008 |
| WO | WO-2008/080056 | 7/2008 |
| WO | WO-2008/090382 | 7/2008 |

(Continued)

OTHER PUBLICATIONS

Carpenter et al., J. Am. Med. Assoc. (2000) 283:381-390. Database PubChem, Accession No. ZINC04827711, Sep. 12, 2005.
Database PubChem, Accession No. CID3315199, Sep. 7, 2005.
Database PubChem, Accession No. ZINC04560769, Sep. 18, 2005.
Database PubChem, Accession No. ZINC04374875, Sep. 13, 2005.
Database PubChem, Accession No. ZINC04908325, Sep. 14, 2005.
Database PubChem, Accession No. ZINC04407915, Sep. 18, 2005.
Finzi et al., Nature Med. (1999) 5:512-517.

(Continued)

Primary Examiner — Kamal Saeed
(74) Attorney, Agent, or Firm — Morrison & Foerster LLP

(57) ABSTRACT

The present invention relates to novel substituted pyrazolamides, methods for their preparation, their use for the treatment and/or prophylaxis of diseases, as well as their use for the manufacture of medicaments for the treatment and/or prophylaxis of diseases, especially of retroviral diseases, in humans and/or animals.

11 Claims, No Drawings

FOREIGN PATENT DOCUMENTS

| | | |
|---|---|---|
| WO | WO-2009/115213 | 9/2009 |
| WO | WO-2009/115252 | 9/2009 |

OTHER PUBLICATIONS

Flexner, Nature Reviews Drug Discovery (2007) 6:959-966.
Genin et al., J. Med. Chem. (2000) 43:1034-1040.
International Search Report for PCT/EP2009/001877, mailed on Feb. 11, 2010, 6 pages.
International Preliminary Report on Patentability for PCT/EP2009/001877, issued on Oct. 5, 2010, 9 pages.
Kavlick and Mitsuya, Antiretroviral Chemotherapy (Hrsg. De Clercq E.) (2001) ASM Press, pp. 279-312.
Medveczky et al., BMC Medicine (2004) 2:34 1-9.
Palella et al., New England Journal of Medicine (1998) 238:853-860.
Ramratnam et al., Nature Med. (2000) 6:82-85.
Richman, Nature (2001) 410:995-1001.
International Search Report for PCT/EP2009/001714, mailed on May 12, 2009, 2 pages.
International Preliminary Report on Patentability for PCT/EP2009/001714, issued on Oct. 5, 2010, 5 pages.
Kort et al., J. Med. Chem. (2008) 51:407-416.
Romero et al., Journal of Medicinal Chemistry (1994) 37:999-1014.
O'Neill, "The Diversity of Retroviral Diseases of the Immune System," Immunology and Cell Biology (1992) 70:193-199.
Van Rompay, "Evaluation of Antiretrovirals in Animal Models of HIV Infection," Antiviral Research (2010) 85:159-175.
West et al., "Targeting HIV-1 Protease: A Test of Drug-Design Methodologies," TIPS (1995) 16:67-75.
Non-Final Office Action for U.S. Appl. No. 12/885,340, mailed May 10, 2012.
Non-Final Office Action for U.S. Appl. No. 13/162,521, mailed Dec. 23, 2011.
Response to Non-Final Office Action for U.S. No. 13/162,521, mailed Mar. 22, 2012.
Supplemental Response to Non-Final Office Action for U.S. Appl. No. 13/162,521, mailed Mar. 29, 2012.
Non-Final Office Action for U.S. Appl. No. 13/162,522, mailed Dec. 21, 2011.
Response to Non-Final Office Action for U.S. Appl. No. 13/162,522, mailed Mar. 20, 2012.
Non-Final Office Action for U.S. Appl. No. 13/162,522 mailed Jun. 22, 2012.
Notice of Allowance for U.S. Appl. No. 13/162,521, mailed Aug. 3, 2012.
Response to Non-Final Office Action for U.S. Appl. No. 12/885,340, mailed Aug. 9, 2012.

SUBSTITUTED PYRAZOLAMIDES AND THEIR USE

CROSS REFERENCE OF RELATED APPLICATIONS

This application is a continuation of pending international application PCT/EP2009/001877, filed Mar. 14, 2009, designating US, which claims priority from German patent application DE 10 2008 015 032.0 filed Mar. 17, 2008. The entire content of these documents is incorporated herein by reference.

BACKGROUND OF THE INVENTION

The present invention relates to novel substituted pyrazolamides, methods for their preparation, their use for the treatment and/or prophylaxis of diseases, as well as their use for the manufacture of medicaments for the treatment and/or prophylaxis of diseases, especially of retroviral diseases, in humans and/or animals.

HIV (human immunodeficiency virus) causes a chronic persistent progressive infection. The disease proceeds via various stages from the asymptomatic infection to the pathological condition AIDS (acquired immunodeficiency syndrome). AIDS is the final stage of the disease caused by infection. The HIV/AIDS disease is characterized by a long clinical latency period with persistent viraemia which, in the final stage, leads to the failure of the immune defences.

The introduction of the anti-HIV combination therapy made it possible in the 1990s to effectively slow the down progression of the disease and thus to prolong substantially the life expectancy of HIV-infected patients (Palella et al., *N. Engl. J. Med.* 1998, 238, 853-860).

The anti-HIV substances currently on the market inhibit the replication of the HI virus by inhibiting the essential viral enzymes reverse transcriptase (RT), protease or the HIV fusion (review in Richman, *Nature* 2001, 410, 995-1001). There are two classes of RT inhibitors: nucleosidic RT inhibitors (NRTI) act through competitive inhibition or chain termination in the DNA polymerization. Non-nucleosidic RT inhibitors (NNRTI) bind allosterically to a hydrophobic pocket in the vicinity of the active centre of the RT and bring about a conformational change in the enzyme. The currently available protease inhibitors (PI) on the other hand block the active centre of the viral protease and thus prevent the maturation newly produced particles into infectious virions.

Since monotherapy with the currently available anti-HIV medicaments leads in a very short time to a failure of the therapy owing to a selection of resistant viruses, usually a combination therapy with several anti-HIV substances from different classes takes place (highly active antiretroviral therapy=HAART; Carpenter et al., *J. Am. Med. Assoc.* 2000, 283, 381-390).

Despite the advances in antiretroviral chemotherapy, recent investigations show that an eradication of HIV and, associated therewith, a cure of the HIV infection is not to be expected with the available medicaments. The latent virus remains in dormant lymphocytes and represents a reservoir for a reactivation and thus for a renewed spread of the virus (Finzi et al., *Nature Med.* 1999, 5, 512-517; Ramratnam et al., *Nature Med.* 2000, 6, 82-85). HIV-infected patients are therefore life-long dependent on an efficient antiviral therapy. Despite combination therapy, a selection of resistant viruses occurs after some time. Since resistance mutations characteristic for each therapeutic class accumulate, the failure of one therapy often means a loss of effect of the complete class of substances. This cross-resistance problem is most pronounced with the class of NNRTIs because in this case a single point mutation in the RT may often be sufficient to bring about a loss of effect of all NNRTIs (review in Kavlick & Mitsuya, *Antiretroviral Chemotherapy* (editor De Clercq E.), 2001, *ASM Press,* 279-312).

The development of resistances is usually favoured by the poor compliance of the patients which is caused by an unfavourable profile of side effects and a complicated dosage regimen for the anti-HIV medicaments.

There is thus a pressing need for novel therapeutic options for controlling an HIV infection. For this purpose, it is important and an urgent aim of HIV therapy research to identify novel chemical lead structures which either address a novel target in the replication of HIV and/or are effective against the growing number of resistant clinical HIV isolates.

U.S. Pat. No. 5,624,941 and EP 576357 describe pyrazoles as cannabinoid receptor antagonists, EP 418845, EP 554829 and WO 04/050632 inter alia for the treatment of inflammatory and thrombotic diseases, WO 03/037274 as sodium ion channel inhibitors for the treatment of pain, WO 06/015860 as adenosine receptor ligands for the treatment of inflammatory and obstructive respiratory diseases, EP 1762568 and EP 1591443 as inhibitors of platelet aggregation, WO 07/002,559 as modulators of the activity of nuclear receptors, WO 07/020,388 and WO 05/080343 as cannabinoid receptor modulators inter alia for the treatment of obesity and psychiatric and neurological disorders, WO 07/009,701 and EP 1743637 for the treatment of cardiovascular risk factors, WO 2005/002576 as inhibitors of various kinases and, DE 10 2004 054 666 for controlling harmful plants or for plant growth regulation.

SUMMARY OF THE INVENTION

One object of the present invention is therefore to provide novel compounds with the same or improved antiviral activity for the treatment of viral infectious diseases in humans and animals which do not have the disadvantages described previously.

It has surprisingly been found that the substituted pyrazolamides described in the present invention have antiviral efficacy.

The invention relates to the use of the compounds of formula

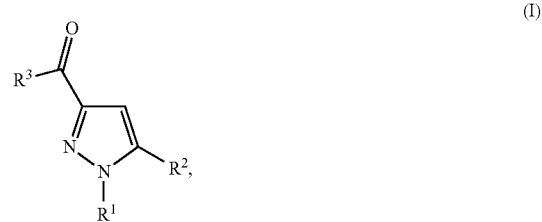

in which
R$^1$ represents phenyl,
  whereby phenyl is substituted with 1 to 3 substituents, whereby the substituents are selected independently of one another from the group consisting of halogen, cyano, nitro, trifluoromethyl, trifluoromethoxy, trifluoromethylthio, (C$_1$-C$_4$)-alkyl and (C$_1$-C$_4$)-alkoxy,
R$^2$ represents phenyl,
  whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^3$ represents a 5- to 8-membered heterocycle bonded via nitrogen, whereby the heterocycle may be substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, and the salts thereof, the solvates thereof and the solvates of the salts thereof, for the manufacture of a medicament for the treatment and/or prophylaxis of retroviral diseases.

Compounds of the invention are the compounds of formula (I) and the salts, solvates and solvates of the salts thereof, as well as the compounds which are encompassed by formula (I) and are mentioned hereinafter as exemplary embodiment(s), and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in the solid or liquid state form a complex by coordination with solvent molecules. Hydrates are a specific form of solvates in which the coordination takes place with water.

In the context of the present invention, the substituents have the following meaning, unless specified otherwise:

Alkyl and the alkyl moieties in alkoxy and alkoxycarbonyl represent straight-chain or branched alkyl and include, unless indicated otherwise, $(C_1-C_6)$-alkyl, in particular $(C_1-C_4)$-alkyl such as, for example, methyl, ethyl, propyl, isopropyl, butyl, isobutyl, Alkoxy for the purpose of the invention represents preferably a straight-chain or branched alkoxy radical in particular having 1 to 6, 1 to 4 or 1 to 3 carbon atoms. A straight-chain or branched alkoxy radical having 1 to 3 carbon atoms is preferred. Mention may be made by way of example and preferably of: methoxy, ethoxy, n-propoxy, isopropoxy, t-butoxy, n-pentoxy and n-hexoxy.

Alkoxycarbonyl represents by way of example and preferably methoxycarbonyl, ethoxycarbonyl, n-propoxycarbonyl, isopropoxycarbonyl, t-butoxycarbonyl, n-pentoxycarbonyl and n-hexoxycarbonyl.

Heterocycle represents a monocyclic heterocyclic radical having 5 to 8, preferably 5 to 6, ring atoms and up to 3, preferably up to 2, heteroatoms and/or hetero groups from the series N, O, S, SO, $SO_2$, whereby a nitrogen atom can also form an N-oxide. The heterocycle may be saturated or partly unsaturated. Preference is given to 5- to 8-membered monocyclic saturated heterocycles having up to two heteroatoms from the series O, N and S, by way of example and preferably 1,4-oxazepanyl, oxetan-3-yl, pyrrolidin-1-yl, pyrrolidin-2-yl, pyrrolidin-3-yl, tetrahydrofuranyl, tetrahydrothienyl, pyranyl, 1,3-thiazolidinyl, piperidin-1-yl, piperidin-2-yl, piperidin-3-yl, piperidin-4-yl, thiopyranyl, morpholin-2-yl, morpholin-3-yl, morpholin-4-yl, thiomorpholin-2-yl, thiomorpholin-3-yl, thiomorpholin-4-yl, perhydroazepinyl, piperazin-1-yl, piperazin-2-yl.

Halogen represents fluorine, chlorine, bromine or iodine, with preference for fluorine and chlorine, unless indicated otherwise.

The radical definitions listed above and indicated in general or in preferred ranges apply both to the final products of formula (I) and correspondingly to the starting materials and intermediates required for the preparation in each case.

The radical definitions indicated specifically in the respective combinations or preferred combinations of radicals are replaced irrespective of the particular combinations of radicals indicated as desired also by radical definitions of other combinations.

The invention also relates to the use of the compounds of formula (I), in which $R^1$ represents phenyl, whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl, whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^3$ represents pyrrolidin-1-yl, morpholin-4-yl, thiomorpholin-4-yl, 1,3-thiazolidin-3-yl, piperidin-1-yl, piperazin-1-yl or 1,4-oxazepan-4-yl, whereby pyrrolidin-1-yl, morpholin-4-yl, thiomorpholin-4-yl, 1,3-thiazolidin-3-yl, piperidin-1-yl, piperazin-1-yl or 1,4-oxazepan-4-yl may be substituted with 1 to 3 substituents, whereby the substituents are selected independently of one another from the group consisting of hydroxy, hydroxymethyl, formyl, amino, oxo, $(C_1-C_4)$-alkyl, $(C_1-C_4)$-alkoxy and $(C_1-C_4)$-alkoxycarbonyl, and the salts thereof, the solvates thereof and the solvates of the salts thereof, for the manufacture of a medicament for the treatment and/or prophylaxis of retroviral diseases.

The invention also relates to the use of the compounds of formula (I), in which $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, and $R^3$ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, or $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of trifluoromethoxy and trifluoromethylthio, and $R^3$ represents an unsubstituted 5- to 8-membered heterocycle bonded via nitrogen,
and the salts thereof, the solvates thereof and the solvates of the salts thereof, for the manufacture of a medicament for the treatment and/or prophylaxis of retroviral diseases.

The invention further relates to compounds of formula (I), in which $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, and $R^3$ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, or $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of trifluoromethoxy and trifluoromethylthio, $R^3$ represents an unsubstituted 5- to 8-membered heterocycle bonded via nitrogen,
and the salts thereof, the solvates thereof and the solvates of the salts thereof.

The invention further relates to compounds of formula (I), in which $R^2$ represents phenyl, whereby phenyl is substituted with a substituent, whereby the substituent is in the meta- or para-position to the site of attachment of the phenyl ring on the pyrazole.

The invention further relates to compounds of formula (I) in which $R^3$ represents pyrrolidin-1-yl, morpholin-4-yl, thiomorpholin-4-yl, 1,3-thiazolidin-3-yl, piperidin-1-yl, piperazin-1-yl or 1,4-oxazepan-4-yl, whereby pyrrolidin-1-yl, morpholin-4-yl, thiomorpholin-4-yl, 1,3-thiazolidin-3-yl, piperidin-1-yl, piperazin-1-yl or 1,4-oxazepan-4-yl may be substituted with 1 to 3 substituents, whereby the substituents are selected independently of one another from the group consisting of hydroxy, hydroxymethyl, formyl, amino, oxo, $(C_1-C_4)$-alkyl, $(C_1-C_4)$-alkoxy and $(C_1-C_4)$-alkoxycarbonyl.

The invention further relates to compounds of formula (I) in which $R^3$ represents pyrrolidin-1-yl, morpholin-4-yl, thiomorpholin-4-yl, 1,3-thiazolidin-3-yl, piperidin-1-yl, piperazin-1-yl or 1,4-oxazepan-4-yl.

The invention further relates to a method for preparing the compounds of formula (I), whereby compounds of formula

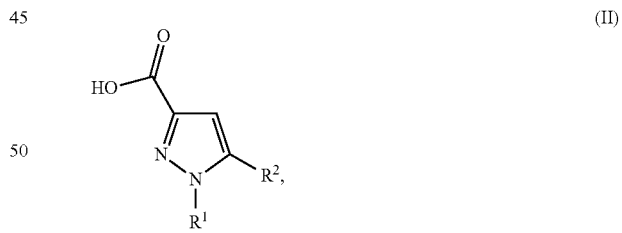

in which
$R^1$ and $R^2$ have the meaning indicated above,
are reacted with compounds of formula

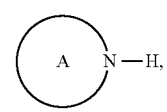

in which
A is a heterocycle as defined previously for $R^3$.

The reaction generally takes place in inert solvents, in the presence of a dehydrating reagent, where appropriate, in the presence of a base, preferably in a temperature range from −30° C. to 50° C. under atmospheric pressure.

Examples of inert solvents are halohydrocarbons such as dichloromethane or trichloromethane, hydrocarbons such as benzene, nitromethane, dioxane, dimethylformamide or acetonitrile. It is likewise possible to use mixtures of the solvents. Dichloromethane or dimethylformamide are particularly preferred.

Examples of bases are alkali-metal carbonates, such as for example sodium or potassium carbonate or bicarbonate, or organic bases such as trialkylamines e.g. triethylamine, N-methylmorpholine, N-methylpiperidine, 4-dimethylaminopyridine or diisopropylethylamine.

Examples of suitable dehydrating reagents in this connection are: carbodiimides, such as for example N,N'-diethyl-N, N'-dipropyl-N,N'-diisopropyl-N,N'-di-cyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methyl-isoxazolium-perchlorate, or acylamino compounds such as 2-ethoxy-1-ethoxycarbonyl-1,2-dihydroquinoline, or propanephosphonic anhydride, or isobutylchloroformate, or bis-(2-oxo-3-oxazolidinyl)-phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures thereof, with bases.

The condensation is preferably carried out with TBTU or with EDC in the presence of HOBt.

In an alternative method the compounds of formula (II) can initially be reacted with thionyl chloride and in the second stage with compounds of formula (III) in the presence of a base, such as for example triethylamine.

The compounds of formula (I) prepared by the methods indicated above carry protecting groups where appropriate, which can be removed, under conditions known to a person skilled in the art, to obtain further compounds of formula (I).

The compounds of formula (III) are known or can be synthesized by known methods from the corresponding starting materials.

The compounds of formula (II) are known and/or can be prepared by hydrolyzing the ester in compounds of formula (IV)

in which
R$^1$ and R$^2$ have the meaning indicated above,
with a base.

The hydrolysis of the ester with a base generally takes place in inert solvents, preferably in a temperature range from room temperature up to reflux of the solvent under atmospheric pressure.

Bases are for example alkali-metal hydroxides such as sodium, lithium or potassium hydroxide, or alkali-metal carbonates such as cesium carbonate, sodium or potassium carbonate, with preferences for lithium or sodium hydroxide.

Examples of inert solvents are halohydrocarbons such as methylene chloride, trichloromethane, tetrachloromethane, trichlorethane, tetrachlorethane, 1,2-dichlorethane or trichloroethylene, ethers such as diethyl ether, methyl-tert-butyl ether, 1,2-dimethoxyethane, dioxane, tetrahydrofuran, glycol dimethyl ether or diethylene glycol dimethyl ether, alcohols such as methanol, ethanol, n-propanol, iso-propanol, n-butanol or tert-butanol, hydrocarbons such as benzene, xylene, toluene, hexane, cyclohexane or petroleum fractions, or other solvents such as dimethylformamide, dimethylacetamide, dimethylsulfoxide, acetonitrile or pyridine, or water, or mixtures of solvents, tetrahydrofuran and/or methanol being preferred as solvents. Potassium hydroxide in methanol is preferred.

The compounds of formula (IV) are known and/or can be prepared by reacting in the first stage compounds of formula (V)

in which
R$^2$ has the meaning indicated above,
with compounds of formula

R$^3$—NH—NH$_2$ (VI), in which
R$^3$ has the meaning indicated above,
and in the second stage heating in acetic acid.

The reaction in the first stage generally takes place in inert solvents, preferably in a temperature range from room temperature to the reflux of the solvent under atmospheric pressure.

Examples of inert solvents are alcohols such as methanol, ethanol, n-propanol, iso-propanol, n-butanol, tert-butanol or 2-methoxyethanol, ethanol being preferred.

The reaction in the second stage in acetic acid generally takes place in a temperature range from room temperature to the reflux of the acetic acid under atmospheric pressure. The reaction can also be carried out in methanol, ethanol or dioxane in a temperature range from room temperature to the reflux of the solvents. Mixtures of methanol, ethanol or dioxane with acetic acid in the ratio from 0.5/99.5 to 99.5/0.5 by volume are suitable. It is also possible to employ mixtures of methanol, ethanol, dioxane or acetic acid with other acids such as for example hydrochloric acid, methanesulfonic acid, p-toluenesulfonic acid, camphorsulfonic acid or trifluoroacetic acid under the conditions mentioned. The reaction is preferably carried out in acetic acid under reflux.

The compounds of formulae (V) and (VI) are known or can be synthesized by known methods from the corresponding starting materials.

The preparation of the compounds of the invention can be illustrated by the following synthesis scheme.

Synthesis Scheme:

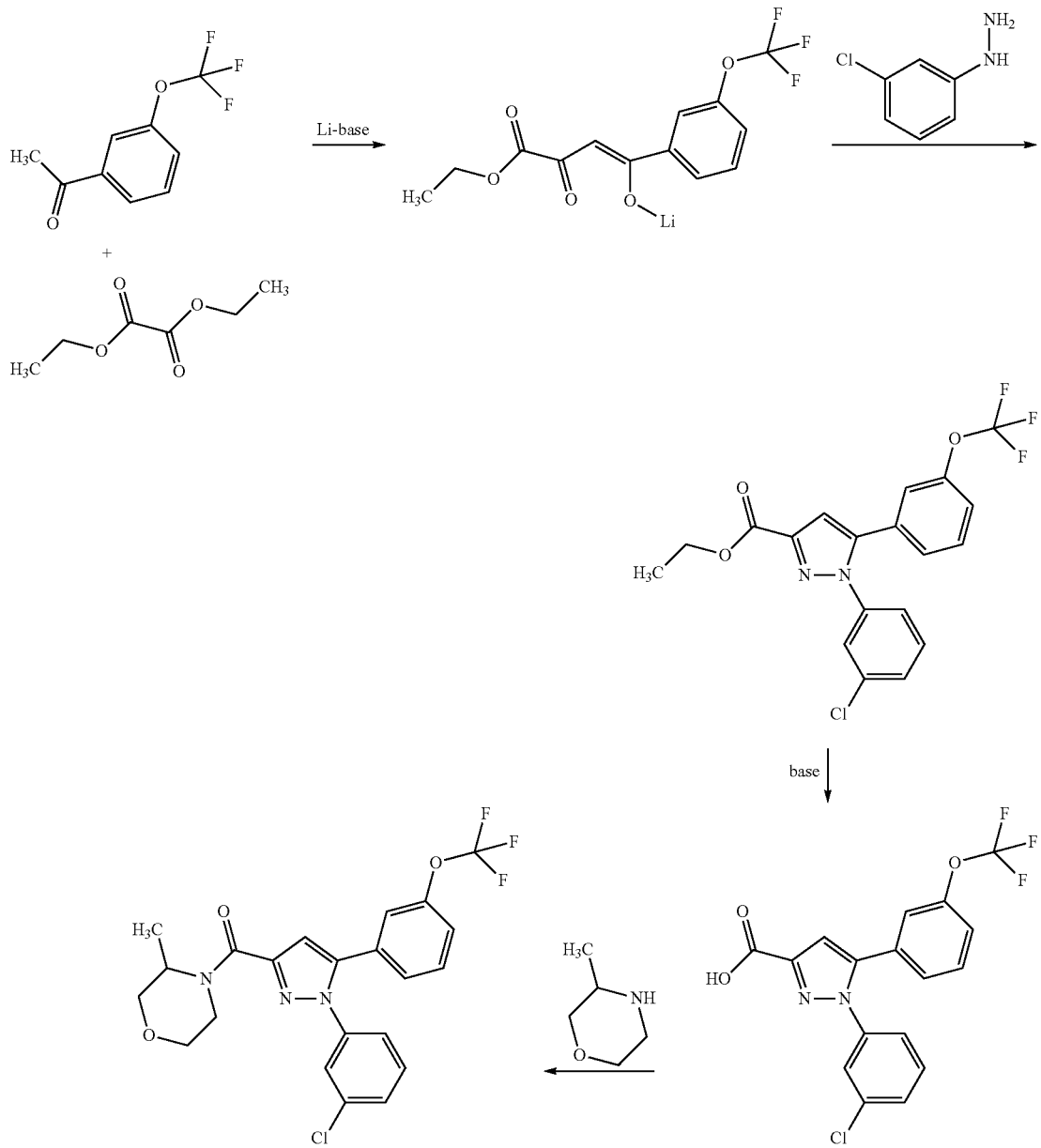

The compounds of the invention show a valuable range of pharmacological effects which could not have been predicted.

They are therefore suitable for use as medicaments for the treatment and/or prophylaxis of diseases in humans and animals.

The compounds of the present invention are distinguished in particular by an advantageous range of antiretroviral effects.

The present invention further relates to the use of the compounds of the invention for the treatment and/or prophylaxis of diseases caused by retroviruses, especially HI viruses.

The present invention further relates to the use of the compounds of the invention for the treatment and/or prophylaxis of diseases, especially of the aforementioned diseases.

The present invention further relates to the use of the compounds of the invention for the manufacture of a medicament for the treatment and/or prophylaxis of diseases, especially of the aforementioned diseases.

The present invention further relates to a method for the treatment and/or prophylaxis of diseases, especially of the aforementioned diseases, using a therapeutically effective amount of the compounds of the invention.

Examples of areas of indication in human medicine which may be mentioned are:

1.) The treatment and prophylaxis of human retroviral infections

2.) The treatment and prophylaxis of infections and diseases (AIDS) caused by HIV I (human immunodeficiency virus; formerly called HTLV III/LAV) and HIV II and the stages associated therewith, such as ARC (AIDS related comlex) and LAS (lymphadenopathy syndrome), as well as the immunodeficiency and encephalopathy caused by this virus.

3.) The treatment of HIV infections caused by mono-, poly- or multiresistant HI viruses.

The expression resistant HI viruses for the purpose of the invention means for example viruses with resistances to nucleosidic inhibitors (RTI), non-nucleosidic inhibitors (NNRTI) or protease inhibitors (PI) or viruses with resistances to other principles of action, e.g. T20 (fusion inhibitors).

4.) The treatment or prophylaxis of the AIDS-carrier state.

5.) The treatment or prophylaxis of an HTLV-I or HTLV-II infection.

Examples of indications in veterinary medicine which may be mentioned are:

Infections with
a) Maedi-visna (in sheep and goats)
b) progressive pneumonia virus (PPV) (in sheep and goats)
c) caprine arthritis encephalitis virus (in sheep and goats)
d) zwoegerziekte virus (in sheep)
e) infectious anaemia virus (of horses)
f) infections caused by the feline leukaemia virus
g) infections caused by the feline immunodeficiency virus (FIV)
h) infections caused by the simian immunodeficiency virus (SIV)

Preference is given from the area of indications in human medicine to items 2, 3 and 4 detailed above.

The substances are particularly suitable for controlling HI viruses showing resistances to known non-nucleosidic inhibitors of the reverse transcriptase, such as, for example, efavirenz or nevirapine.

The present invention further relates to medicaments comprising at least one compound of the invention and at least one or more further active ingredients, in particular for the treatment and/or prophylaxis of the aforementioned diseases.

The compounds of the invention can also, especially in items 2, 3 and 4 detailed above, advantageously be employed as components of a combination therapy with one or more other compounds which are active in these areas of application. These compounds can for example be employed in combination with effective doses of substances having antiviral activity based on the principles of action detailed below:

HIV protease inhibitors; examples which may be mentioned are: saquinavir, indinavir, ritonavir, nelfinavir, amprenavir, lopinavir, atazanavir, fosamprenavir, tipranavir, darunavir; nucleosidic, nucleotidic and non-nucleosidic inhibitors of the HIV reverse transcriptase; examples which may be mentioned are: zidovudine, lamivudine, didanosine, zalcitabine, stavudine, lamivudine, abacavir, tenofovir, adefovir, emtricitabine, amdoxovir, apricitabine, racivir, nevirapine, delavirdine, efavirenz, etravirine, rilpivirine, UK-453,061; HIV integrase inhibitors, examples which may be mentioned are: raltegravir, elvitegravir; HIV fusion inhibitors; an example which may be mentioned is: enfuvirtide; inhibitors of the CXCR4/CCR5/gp120 interaction; examples which may be mentioned are: maraviroc, vicriviroc, INCB009471, AMD-070; inhibitors of the polyprotein maturation; an example which may be mentioned is: bevirimat.

This selection is intended to serve to illustrate the possible combinations but not to restrict to the examples detailed here. In principle, every combination of the compounds of the invention with substances having antiviral activity is to be considered as within the scope of the invention.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, otically or as an implant or stent.

For these administration routes the compounds of the invention can be administered in suitable administration forms.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other administration a routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as for example patches), milk, pastes, foams, dusting powders, implants or stents.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, usually together with one or more inert, non-toxic, pharmaceutically acceptable excipients, as well as to their use for the aforementioned purposes.

It has generally proved to be advantageous both in human and in veterinary medicine to administer the active ingredient(s) of the invention in total amounts of from 0.1 to 200 mg/kg, preferably 1 to 100 mg/kg, of body weight every 24 hours, where appropriate in the form of a plurality of single doses, to achieve the desired result. A single dose preferably comprises the active ingredient(s) in amounts of from 1 to 80 mg/kg, in particular 1 to 30 mg/kg, of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. In the case of an administration of larger amounts, it may be advisable to distribute these in a plurality of single doses over the day.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

DETAILED DESCRIPTION OF PREFERRED EMBODIMENTS

A) Examples

Abbreviations:

| | |
|---|---|
| aq. | aqueous, aqueous solution |
| conc. | concentrated |
| DCI | direct chemical ionization (in MS) |
| DMA | N,N-dimethylacetamide |
| DMF | N,N-dimethylformamide |
| DMSO | dimethyl sulfoxide |
| EDC | N'-(3-dimethylaminopropyl)-N-ethylcarbodiimide × HCl |
| eq. | equivalent(s) |
| ESI | electrospray ionization (in MS) |
| h | hour(s) |
| HATU | O-(7-azabenzotriazol-1-yl)-N,N,N',N'-tetramethyluronium hexafluorophosphate |
| HPLC | high pressure, high performance liquid chromatography |
| LC-MS | coupled liquid chromatography-mass spectrometry |
| min | minute(s) |
| MS | mass spectrometry |
| NMR | nuclear magnetic resonance spectroscopy |
| PyBOP | benzotriazol-1-yloxytris(pyrrolidino)phosphonium hexafluorophosphate |
| $R_t$ | retention time (in HPLC) |
| RT | room temperature |
| TBTU | O-(benzotriazol-1-yl)-N,N,N',N'-tetramethyluronium tetrafluoroborate |
| TFA | trifluoroacetic acid |
| THF | tetrahydrofuran |
| TMOF | trimethyl orthoformate |

HPLC Methods:

Method 1: Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→6.5 min 90% B→6.7 min 2% B→>7.5 min 2% B; flow rate: 0.75 ml/min; temperature: 30° C.; UV detection: 210 nm Method 2: Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→9 min 90% B→9.2 min 2% B→10 min 2% B; flow rate: 0.75 ml/min; temperature: 30° C.; UV detection: 210 nm Method 3: Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→15 min 90% B→15.2 min 2% B→16 min 2% B; flow rate: 0.75 ml/min; temperature: 30° C.; UV detection: 210 nm LC/MS Methods:

Method 1: MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm Method 2: MS instrument type: Micromass ZQ; HPLC instrument type: HP 1100 Series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm Method 3: Instrument: Micromass Quattro LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm Method 4: MS instrument: Micromass TOF (LCT); HPLC instrument: 2 connected columns, Waters 2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A; oven: 40° C.; flow rate: 3.0 ml/min; UV detection: 210 nm.

Starting Compounds

Example 1A

Lithium (1Z)-4-ethoxy-3,4-dioxo-1-[3-(trifluoromethyl)phenyl]but-1-en-1-olate

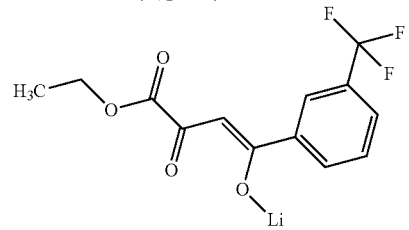

A solution of 5.7 ml (5.7 mmol) of lithium hexamethyldisilazide (solution in hexane) in diethyl ether is provided at −78° C. 1 g (5.31 mmol) of 3-(trifluoromethyl)acetophenone is dissolved in 6 ml of diethyl ether and added dropwise. After 45 minutes at −78° C., 0.79 ml (5.85 mmol) of diethyl oxalate are added dropwise and the mixture is stirred for 12 hours at RT. The reaction mixture is evaporated to half the volume and the solid obtained is collected by suction filtration. The crystals are washed with diethyl ether and dried in vacuum. 1.26 g (4.3 mmol, 81% yield of theory) are obtained as product. The product obtained is used directly in the next stage.

Example 2A

Lithium (1Z)-4-ethoxy-3,4-dioxo-1-{3-[(trifluoromethyl)thio]phenyl}but-1-en-1-olate

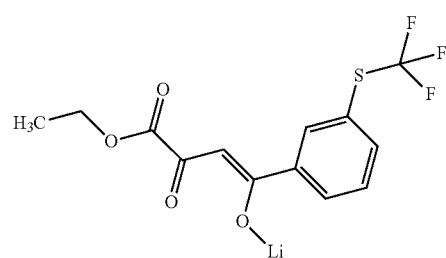

Starting from 1 g (4.54 mmol) of 3-(trifluoromethylthio)acetophenone and 0.68 ml (5 mmol) of diethyl oxalate, 1.22 g (3.7 mmol, 82% yield of theory) are obtained as product according to the method described in example 1A. The product obtained is used directly in the next stage.

Example 3A

Lithium (1Z)-4-ethoxy-3,4-dioxo-1-[3-(trifluoromethoxy)phenyl]but-1-en-1-olate

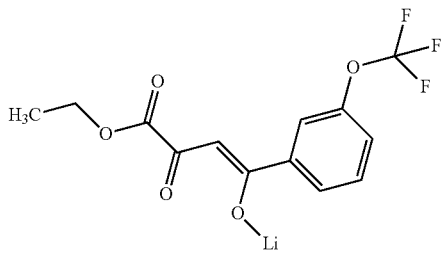

Starting from 5 g (24.5 mmol) of 1-[3-(trifluoromethoxy)phenyl]ethan-1-one and 3.66 ml (26.9 mmol) of diethyl oxalate, 4.53 g (14.6 mmol, 60% yield of theory) are obtained as product according to the method described in example 1A. The product obtained is used directly in the next stage.

Example 4A

Ethyl 1-(3-chlorophenyl)-5-[3-(trifluoromethyl)phenyl]-1H-pyrazole-3-carboxylate

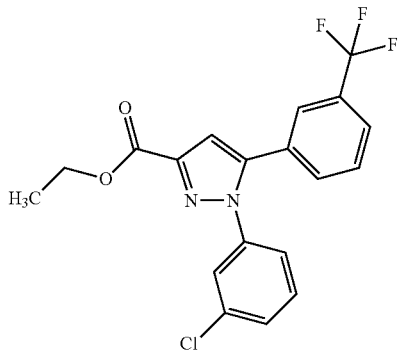

631.5 mg (2.15 mmol) of lithium (1Z)-4-ethoxy-3,4-dioxo-1-[3-(trifluoromethyl)phenyl]but-1-en-1-olate from example 1A are suspended in 15 ml of ethanol, 522.7 mg (2.92 mmol) of 3-chlorophenylhydrazine hydrochloride are added and the mixture is stirred for 48 hours at room temperature. The reaction mixture is concentrated by evaporation to approx. 5 ml and the precipitated solid is collected by suction filtration. After drying the crystals, they are taken up in 15 ml of acetic acid and stirred for 12 hours under reflux. The mixture is added to ethyl acetate, and washed with water, a saturated sodium bicarbonate solution and a sodium chloride solution. The organic phase is dried over sodium sulfate and concentrated on a rotary evaporator. The residue obtained is purified on a silica gel flash (mobile phase: cyclohexane/ethyl acetate 3:1) and then crystallized from diethyl ether/pentane. 528 mg (1.5 mmol, 62% yield of theory) of product are obtained.

Melting point: 114° C.
HPLC (method 1): $R_f$=5.39 min
MS (ESIpos): m/z=395 (M+H)$^+$
$^1$H-NMR (400 MHz, DMSO-d$_6$): δ=7.78 (d, 1H), 7.68-7.54 (m, 5H), 7.5 (t, 1H), 7.35 (s, 1H), 7.29 (d, 1H), 4.36 (q, 2H), 1.33 (t, 3H).

Example 5A

Ethyl 1-(3-chlorophenyl)-5-{3-[trifluoromethyl)thio]phenyl}-1H-pyrazole-3-carboxylate

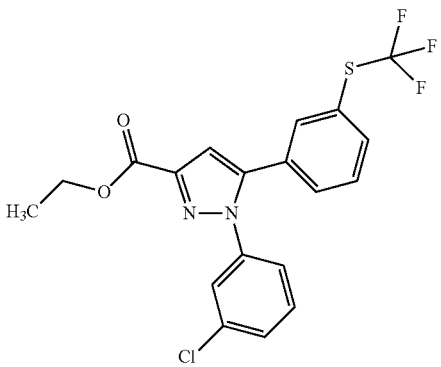

Starting from 1.22 g (3.74 mmol) of lithium (1Z)-4-ethoxy-3,4-dioxo-1-{3-[(trifluoromethyl)thio]phenyl}-but-1-en-1-olate from example 2A and 568.35 mg (3.63 mmol) of (3-chlorobenzyl)hydrazine, 845.1 mg (2.1 mmol, 77% yield of theory) of product are obtained according to the method described in example 4A.

Melting point: 95° C.
HPLC (method 1): $R_f$=5.58 min
MS (ESIpos): m/z=427 (M+H)+
$^1$H-NMR (300 MHz, DMSO-d$_6$): δ=7.75 (d, 1H), 7.7-7.42 (m, 6H), 7.33-7.22 (m, 2H), 4.36 (q, 2H), 1.32 (t, 3H).

Example 6A

Ethyl 1-(3-Chlorophenyl)-5-[3-(trifluoromethoxy)phenyl]-1H-pyrazole-3-carboxylate

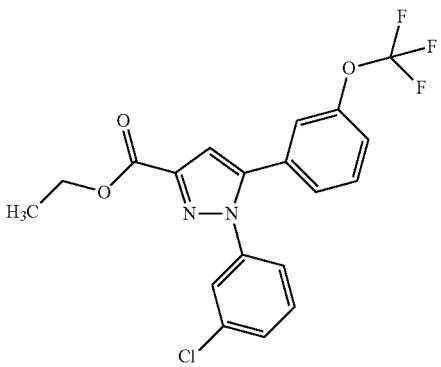

Starting from 4.53 g (14.6 mmol) of lithium (1Z)-4-ethoxy-3,4-dioxo-1-[3-(trifluoro-methoxy)phenyl]but-1-en-1-olate from example 3A and 3.56 g (19.8 mmol) of 3-chlorophenylhydrazine hydrochloride, 1.98 g (4.8 mmol, 33% yield of theory) of product are obtained according to the method described in example 4A.

Melting point: 87° C.
HPLC (method 1): $R_f$=5.38 min
MS (ESIpos): m/z=411 (M+H)+

$^1$H-NMR (400 MHz, DMSO-d$_6$): δ=7.6-7.45 (m, 4H), 7.4 (d, 2H), 7.34-7.25 (m, 2H), 7.2 (s, 1H), 4.35 (q, 2H), 1.32 (t, 3H).

Example 7A 1-(3-Chlorophenyl)-5-[3-(trifluoromethyl)phenyl]-1H-pyrazole-3-carboxylic acid

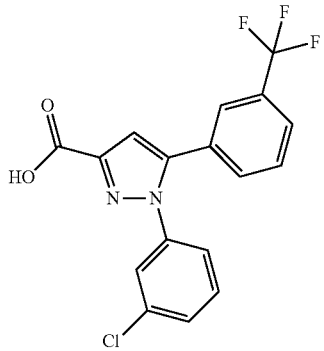

8.5 g (152 mmol) of potassium hydroxide are added to a solution of 6 g (15.2 mmol) of ethyl 1-(3-chlorophenyl)-5-[3-(trifluoromethyl)phenyl]-1H-pyrazole-3-carboxylate from example 4A in 80 ml of methanol and the mixture is stirred for 30 minutes under reflux. The reaction mixture is diluted with water and rendered acidic using 1 molar hydrochloric acid. The mixture is extracted with ethyl acetate. The organic phase is washed with a sodium chloride solution, dried over sodium sulfate and concentrated on a rotary evaporator. The residue obtained is crystallized from diethyl ether/pentane. The crystals are collected by suction filtration, washed with a little pentane and dried. 5.2 g (14.2 mmol, 93% yield of theory) of product are obtained.

HPLC (method 2): R$_t$=4.57 min

MS (ESIpos): m/z=367 (M+H)+

$^1$H-NMR (300 MHz, DMSO-d$_6$): δ=13.15 (s, 1H), 7.78 (d, 1H), 7.68-7.43 (m, 6H), 7.3-7.23 (m, 2H).

Example 8A 1-(3-Chlorophenyl)-5-{3-[(trifluoromethyl)thio]phenyl}-1H-pyrazole-3-carboxylic acid

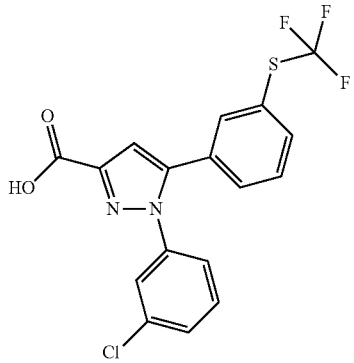

Starting from 850 mg (1.99 mmol) of ethyl 1-(3-chlorophenyl)-5-{3-[(trifluoromethyl)thio]phenyl}-1H-pyrazole-3-carboxylate from example 5A and 1.12 g (19.9 mmol) of potassium hydroxide, 691.5 mg (1.7 mmol, 87% yield of theory) are obtained as crystals according to the method described in example 7A.

Melting point: 148° C.

HPLC (method 1): R$_t$=4.91 min

MS (ESIpos): m/z=399 (M+H)+

$^1$H-NMR (300 MHz, DMSO-d$_6$): δ=13.15 (s, 1H), 7.74 (d, 1H), 7.7-7.42 (m, 6H), 7.3 (d, 1H), 7.2 (s, 1H).

Example 9A 1-(3-Chlorophenyl)-5-[3-(trifluoromethoxy)phenyl]-1H-pyrazole-3-carboxylic acid

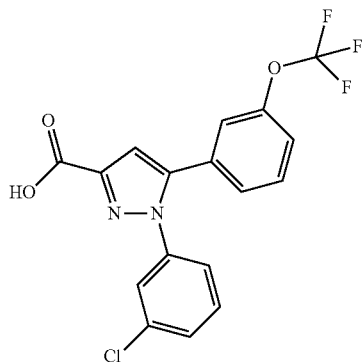

Starting from 1.9 g (4.63 mmol) of ethyl 1-(3-chlorophenyl)-5-[3-(trifluoromethoxy)phenyl]-1H-pyrazole-3-carboxylate from example 6A and 2.59 g (46.25 mmol) of potassium hydroxide, 1.68 g (4.4 mmol, 95% yield of theory) are obtained as crystals according to the method described in example 7A.

HPLC (method 2): R$_t$=4.76 min $^1$H-NMR (400 MHz, DMSO-d$_6$): δ=7.6-7.45 (m, 4H), 7.44-7.38 (m, 2H), 7.28 (d, 1H), 7.2 (d, 2H).

Example 10A

Lithium (1Z)-1-(3-cyanophenyl)-4-ethoxy-3,4-dioxobut-1-en-1-olate

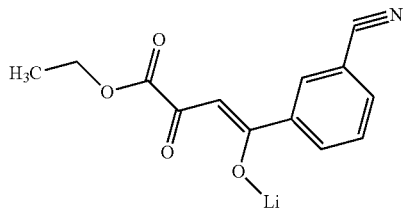

Starting from 5 g (34.4 mmol) of 3-acetylbenzonitrile and 5.15 ml (37.9 mmol) of diethyl oxalate, 5.49 g (21.9 mmol, 63% yield of theory) are obtained as product according to the method described in example 1A. The product obtained is used directly in the next stage.

Example 11A 4-(2,4-Dichlorophenyl)-2,4-dioxobutanoic acid ethyl ester

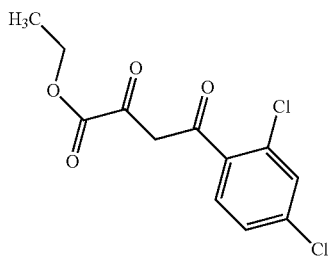

The preparation takes place according to Bioorganic & Medicinal Chemistry Letters 12 (16), 2133 (2002).

Example 12A 4-(3,4-Dimethoxyphenyl)-2,4-dioxobutanoic acid ethyl ester

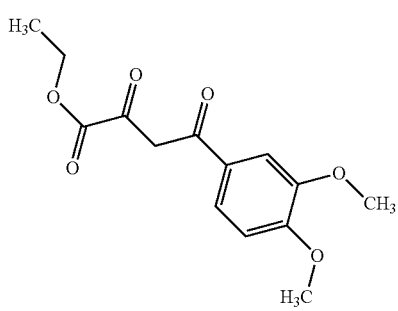

The preparation takes place according to Bioorganic & Medicinal Chemistry Letters 12 (16), 2133 (2002).

Example 13A 2,4-Dioxo-4-phenylbutanoic acid ethyl ester

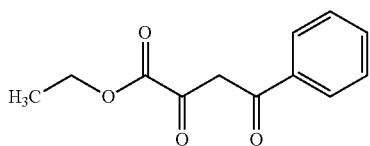

The preparation takes place according to A. Roy and S. Batra, Synthesis (15), 2325 (2003).

Example 14A 3-(3-Nitrophenyl)-3-oxopropanoic acid ethyl ester

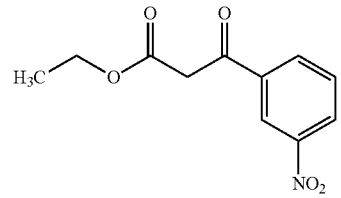

The preparation takes place according to Tetrahedron 60(31), 6479 (2004).

Example 15A

Ethyl 1-(4-methylphenyl)-5-[3-(trifluoromethyl)phenyl]-1H-pyrazole-3-carboxylate

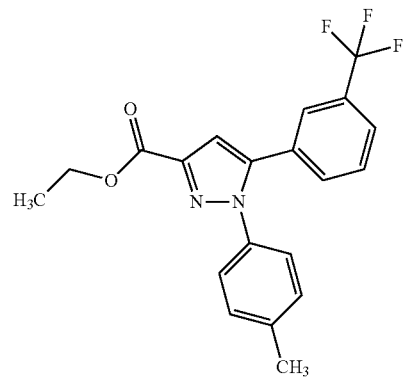

Starting from 631.5 mg (2.15 mmol) of lithium (1Z)-4-ethoxy-3,4-dioxo-1-[3-(trifluoromethyl)phenyl]but-1-en-1-olate from example 1A and 463.2 mg (2.92 mmol) of 4-tolyl-hydrazine hydrochloride, 535.8 mg (1.4 mmol, 67% yield of theory) of product are obtained according the method described in example 4A.

Melting point: 102° C.

HPLC (method 1): $R_t$=5.36 min

MS (ESIpos): m/z=375 (M+H)+

$^1$H-NMR (400 MHz, DMSO-d$_6$): δ=7.73 (d, 1H), 7.64-7.5 (m, 3H), 7.32-7.2 (m, 5H), 4.33 (q, 2H), 2.36 (s, 3H), 1.32 (t, 3H).

Example 16A

Ethyl 1-(3-chlorophenyl)-5-(3-cyanophenyl)-1H-pyrazole-3-carboxylate

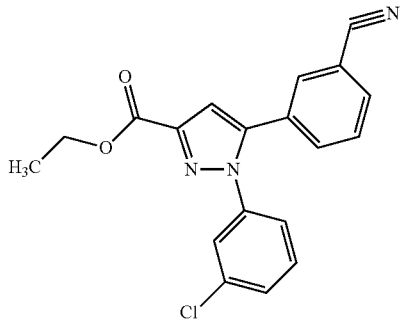

Starting from 10 g (39.81 mmol) of lithium (1Z)-1-(3-cyanophenyl)-4-ethoxy-3,4-dioxobut-1-en-1-olate from example 10A and 9.7 g (54.15 mmol) of 3-chlorophenylhydrazine hydrochloride, 4.97 g (14 mmol, 35% yield of theory) of product are obtained according to the method described in example 4A.

Melting point: 101° C.

LC-MS (method 1): $R_t$=2.45 min

MS (ESIpos): m/z=352 (M+H)+

$^1$H-NMR (400 MHz, DMSO-$d_6$): δ=7.38 (d, 2H), 7.6-7.43 (m, 5H), 7.3 (s, 1H), 7.28 (d, 1H), 4.35 (q, 2H), 1.32 (t, 3H).

Example 17A

Ethyl 1-(3-chlorophenyl)-5-(3,4-dimethoxyphenyl)-1H-pyrazole-3-carboxylate

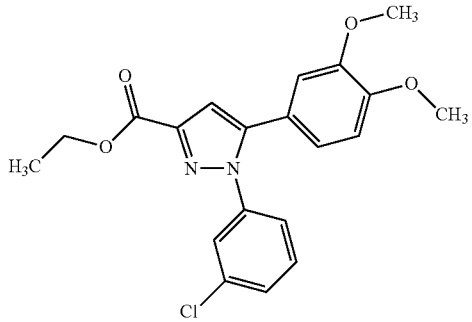

Starting from 1 g (3.57 mmol) of 4-(3,4-dimethoxyphenyl)-2,4-dioxobutanoic acid ethyl ester from example 12A and 868.8 mg (4.85 mmol) of 3-chlorophenylhydrazine hydrochloride, 1.03 g (2.7 mmol, 74% yield of theory) of product are obtained according to the method described in example 4A and after purification by preparative HPLC.

Melting point: 99° C.

HPLC (method 2): $R_t$=4.81 min

MS (ESIpos): m/z=387 (M+H)+

$^1$H-NMR (400 MHz, DMSO-$d_6$): δ=7.57-7.44 (m, 3H), 7.27 (d, 1H), 7.13 (s, 1H), 6.95 (d, 1H), 6.88 (s, 1H), 6.77 (d, 1H), 4.34 (q, 2H), 3.75 (s, 3H), 3.62 (s, 3H), 1.32 (t, 3H).

Example 18A

Ethyl 1-(3-chlorophenyl)-5-(2,4-dichlorophenyl)-1H-pyrazole-3-carboxylate

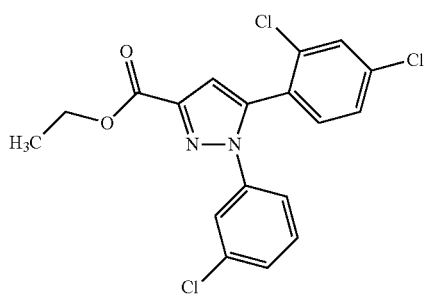

Starting from 1 g (3.46 mmol) of 4-(2,4-dichlorophenyl)-2,4-dioxobutanoic acid ethyl ester from example 11A and 842.25 mg (4.7 mmol) of 3-chlorophenylhydrazine hydrochloride, 297.5 mg (0.75 mmol, 22% yield of theory) of product are obtained according to the method described in example 4A and after purification by preparative HPLC.

Melting point: 87° C.

HPLC (method 2): $R_t$=5.49 min $^1$H-NMR (400 MHz, DMSO-$d_6$): δ=7.75 (s, 1H), 7.63-7.54 (m, 2H), 7.52-7.39 (m, 3H), 7.2-7.1 (m, 2H), 4.35 (q, 2H), 1.33 (t, 3H).

Example 19A

Ethyl 1-(3-chlorophenyl)-5-phenyl-1H-pyrazole-3-carboxylate

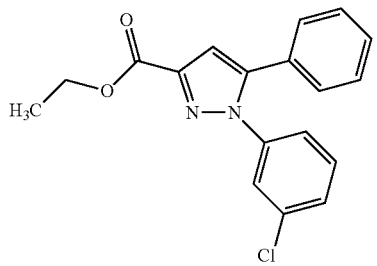

Preparation takes place according to Il Farmaco 59(11), 849 (2004).

Example 20A

Ethyl 1-(3-chlorophenyl)-5-(3-nitrophenyl)-1H-pyrazole-3-carboxylate

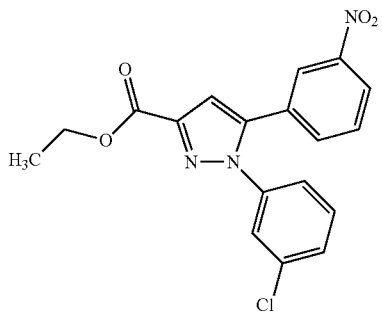

Starting from 1 g (3.77 mmol) of 3-(3-nitrophenyl)-3-oxo-propanoic acid ethyl ester from example 14A and 918.13 mg (5.13 mmol) of 3-chlorophenylhydrazine hydrochloride, 874.5 mg (2.4 mmol, 62% yield of theory) of product are obtained according to the method described in example 4A and after purification by preparative HPLC.

Melting point: 116° C.

HPLC (method 2): $R_f$=5.33 min

MS (ESIpos): m/z=372 (M+H)+

$^1$H-NMR (400 MHz, DMSO-$d_6$): δ=8.39 (d, 1H), 8.3 (s, 1H), 7.89-7.78 (m, 2H), 7.78-7.68 (m, 2H), 7.63 (t, 1H), 7.53 (s, 1H), 7.46 (d, 1H).

Example 21A

Ethyl 1-(3-methoxyphenyl)-5-[3-(trifluoromethyl)phenyl]-1H-pyrazole-3-carboxylate

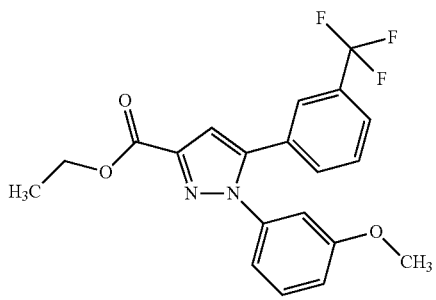

Starting from 1.5 g (5.2 mmol) of lithium (1Z)-4-ethoxy-3,4-dioxo-1-[3-(trifluoro-methyl)phenyl]but-1-en-1-olate from example 1A and 1 g (5.73 mmol) of 3-methoxyphenyl-hydrazine hydrochloride, 1.73 g (4.4 mmol, 85% yield of theory) of product are obtained according to the method described in example 4A and after purification on silica gel (flash chromatography).

LC-MS (method 2): $R_t$=2.95 min

MS (ESIpos): m/z=391 (M+H)+

$^1$H-NMR (400 MHz, CDCl$_3$): δ=7.59 (d, 1H), 7.53 (s, 1H), 7.43 (t, 1H), 7.37 (d, 1H), 7.28-7.14 (m, 2H), 6.93 (s, 2H), 6.8 (d, 1H), 4.46 (q, 2H), 3.75 (s, 3H), 1.43 (t, 3H).

Example 22A 1-(4-Methylphenyl)-5-[3-(trifluoromethyl)phenyl]-1H-pyrazole-3-carboxylic acid

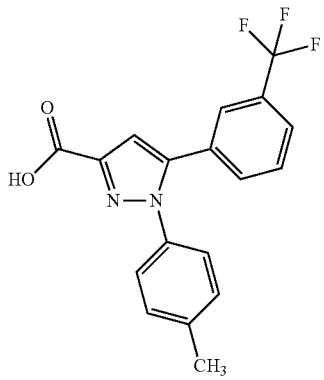

Starting from 450 mg (1.2 mmol) of ethyl 1-(4-methylphenyl)-5-[3-(trifluoro-methyl)phenyl]-1H-pyrazole-3-carboxylate from example 15A and 135 mg (2.4 mmol) of potassium hydroxide, 334.7 mg (0.97 mmol, 80% yield of theory) are obtained as crystals according to method described in example 7A.

Melting point: 151° C.

HPLC (method 1): $R_t$=4.69 min

MS (ESIpos): m/z=347 (M+H)+

$^1$H-NMR (300 MHz, DMSO-$d_6$): δ=13.08 (s, 1H), 7.72 (d, 1H), 7.63-7.5 (m, 3H), 7.31-7.18 (m, 5H), 2.35 (s, 3H).

Example 23A 1-(3-Chlorophenyl)-5-(3-cyanophenyl)-1H-pyrazole-3-carboxylic acid

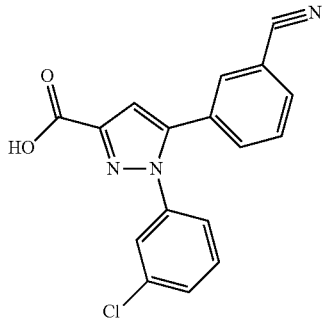

Starting from 2.75 g (7.82 mmol) of ethyl 1-(3-chlorophenyl)-5-(3-cyanophenyl)-1H-pyrazole-3-carboxylate from example 16A and 4.39 g (78.2 mmol) of potassium hydroxide, 2.37 mg (7.3 mmol, 94% yield of theory) are obtained as crystals according to the method described in example 7A.

HPLC (method 1): $R_t$=4.20 min

MS (ESIpos): m/z=324 (M+H)+

¹H-NMR (400 MHz, DMSO-d$_6$): δ=13.15 (s, 1H), 7.91-7.84 (m, 2H), 7.62-7.43 (m, 5H), 7.27-7.22 (m, 2H).

Example 24A 1-(3-Chlorophenyl)-5-phenyl-1H-pyrazole-3-carboxylic acid

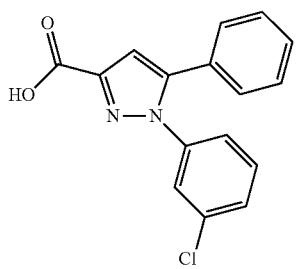

Starting from 400 mg (1.22 mmol) of ethyl 1-(3-chlorophenyl)-5-phenyl-1H-pyrazole-3-carboxylate from example 19A and 686.8 mg (12.24 mmol) of potassium hydroxide, 335.8 mg (1.1 mmol, 92% yield of theory) are obtained as crystals according to the method described in example 7A.

Melting point: 187° C.

HPLC (method 2): R$_t$=4.40 min

MS (ESIpos): m/z=299 (M+H)+

¹H-NMR (400 MHz, DMSO-d$_6$): δ=13.06 (s, 1H), 7.55-7.35 (m, 6H), 7.33-7.2 (m, 3H), 7.08 (s, 1H).

Example 25A 1-(3-Chlorophenyl)-5-(3,4-dimethoxyphenyl)-1H-pyrazole-3-carboxylic acid

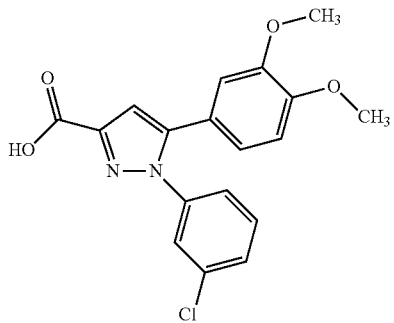

Starting from 500 mg (1.29 mmol) of ethyl 1-(3-chlorophenyl)-5-(3,4-dimethoxy-phenyl)-1H-pyrazole-3-carboxylate from example 17A and 725.2 mg (12.9 mmol) of potassium hydroxide, 434.1 mg (1.2 mmol, 94% yield of theory) are obtained as crystals according to the method described in example 7A.

Melting point: 161° C.

HPLC (method 2): R$_t$=4.15 min

MS (ESIpos): m/z=359 (M+H)$^+$

¹H-NMR (400 MHz, DMSO-d$_6$): δ=13.1 (s, 1H), 7.57-7.42 (m, 3H), 7.26 (d, 1H), 7.06 (s, 1H), 6.95 (d, 1H), 6.86 (s, 1H), 6.78 (d, 1H), 5.57 (s, 3H), 3.61 (s, 3H).

Example 26A 1-(3-Chlorophenyl)-5-(2,4-dichlorophenyl)-1H-pyrazole-3-carboxylic acid

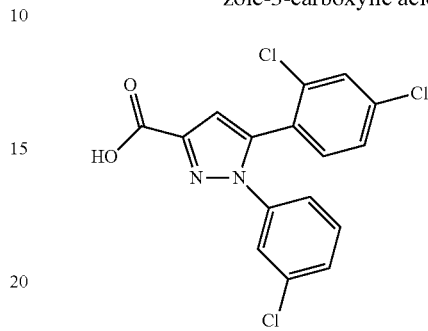

Starting from 240 mg (0.61 mmol) of ethyl 1-(3-chlorophenyl)-5-(2,4-dichloro-phenyl)-1H-pyrazole-3-carboxylate from example 18A and 340.3 mg (6.1 mmol) of potassium hydroxide, 204 mg (0.55 mmol, 92% yield of theory) are obtained as crystals according to the method described in example 7A.

Melting point: 191° C.

HPLC (method 2): R$_t$=4.87 min

¹H-NMR (400 MHz, DMSO-d$_6$): δ=13.17 (s, 1H), 7.75 (s, 1H), 7.63-7.52 (m, 2H), 7.52-7.36 (m, 3H), 7.16 (d, 1H), 7.07 (s, 1H).

Example 27A 1-(3-Chlorophenyl)-5-(3-nitrophenyl)-1H-pyrazole-3-carboxylic acid

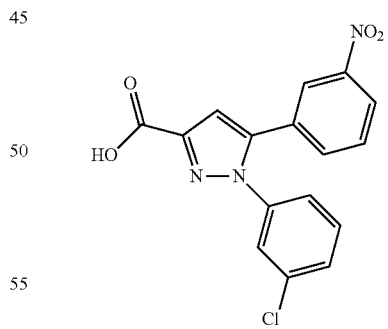

Starting from 400 mg (1.1 mmol) of ethyl 1-(3-chlorophenyl)-5-(3-nitrophenyl)-1H-pyrazole-3-carboxylate from example 20A and 603 mg (10.7 mmol) of potassium hydroxide, 340.5 mg (0.99 mmol, 92% yield of theory) are obtained as crystals according to the method described in example 7A.

Melting point: 187° C.

HPLC (method 2): R$_t$=4.37 min

MS (ESIpos): m/z=344 (M+H)+

$^1$H-NMR (400 MHz, DMSO-$d_6$): δ=13.16 (s, 1H), 8.24 (d, 1H), 8.14 (s, 1H), 7.77-7.41 (m, 5H), 7.36-7.21 (m, 2H).

Example 28A 1-(3-Methoxyphenyl)-5-[3-(trifluoromethyl)phenyl]-1H-pyrazole-3-carboxylic acid

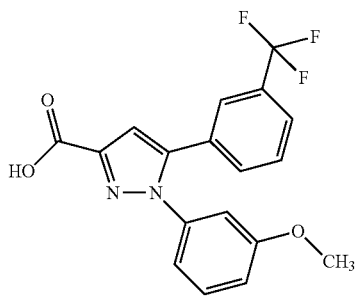

Starting from 1.6 g (4.1 mmol) of ethyl 1-(3-methoxyphenyl)-5-[3-(trifluoromethyl)phenyl]-1H-pyrazole-3-carboxylate from example 21A and 2.3 g (41 mmol) of potassium hydroxide, 1.07 g (2.9 mmol, 72% yield of theory) are obtained as crystals according to the method described in example 7A.

Melting point: 154° C.

LC-MS (method 3): $R_t$=2.37 min

MS (ESIpos): m/z=363 (M+H)+

$^1$H-NMR (400 MHz, DMSO-$d_6$): δ=7.77-7.71 (m, 1H), 7.65-7.57 (m, 3H), 7.36 (t, 1H), 7.25 (s, 1H), 7.07-7.02 (m, 1H), 6.96 (s, 1H), 6.86 (d, 1H), 3.71 (s, 3H).

Exemplary Embodiments

Example 1

4-({1-(3-Chlorophenyl)-5-[3-(trifluoromethyl)phenyl]-1H-pyrazol-3-yl}carbonyl)-morpholine

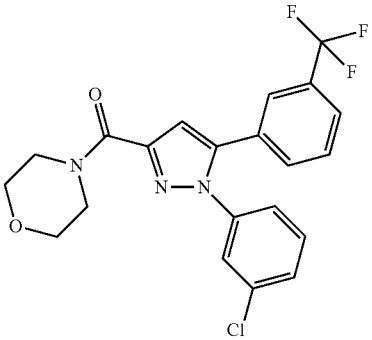

Under exclusion of oxygen, 0.06 ml (0.82 mmol) of thionyl chloride are added to a solution of 100 mg (0.27 mmol) of 1-(3-chlorophenyl)-5-[3-(trifluoromethyl)phenyl]-1H-pyrazole-3-carboxylic acid from example 9A in 3 ml of toluene, and the mixture is stirred for 3 hours under reflux. After cooling, the reaction mixture is concentrated on a rotary evaporator. The obtained intermediate is taken up in 2 ml of dichloromethane and the mixture is cooled to approx. 0° C. 0.06 ml (0.44 mmol) of triethylamine and 0.04 ml (0.44 mmol) of morpholine are added, and the mixture is stirred for a further 12 hours at room temperature. The reaction mixture is added to ethyl acetate and the mixture is washed twice with a sodium chloride solution. The organic phase is dried over sodium sulfate and concentrated on a rotary evaporator. The obtained residue is separated by silica gel flash (mobile phase: cyclohexane/ethyl acetate 1:1). The obtained oil is crystallized from diethyl ether/pentane. The crystals are collected by suction filtration and dried. 92.8 mg (0.21 mmol, 78% yield of theory) of product are obtained.

HPLC (method 1): $R_t$=4.87 min

MS (ESIpos): m/z=436 (M+H)+

$^1$H-NMR (300 MHz, DMSO-$d_6$): δ=7.77 (d, 1H), 7.68-7.42 (m, 6H), 7.28 (d, 1H), 7.15 (s, 1H), 4.0 (s, 2H), 3.75-3.57 (m, 6H).

The following compounds are prepared in analogy to example 1:

| Ex. No. | Structure | Prepared from yield | Analytical data HPLC/LC-MS (method) MS, $^1$H-NMR |
|---|---|---|---|
| 2 | (structure shown) | Example 7A 43 mg, 72% of theory | HPLC (1): $R_t$ = 2.22 min<br>MS (ESIpos): m/z = 436 (M + H)+<br>$^1$H-NMR(300 MHz, CDCl$_3$):<br>δ = 7.62 (d, 1H), 7.55-7.28 (m, 6H),<br>7.16-7.01 (m, 2H), 4.66-4.55 (m, 1H),<br>4.21-4.08 (m, 2H), 3.95-3.75 (m, 2H),<br>2.17-1.95 (m, 2H). |

| Ex. No. | Structure | Prepared from yield | Analytical data HPLC/LC-MS (method) MS, ¹H-NMR |
|---|---|---|---|
| 3 | (structure: 5-[3-(trifluoromethylthio)phenyl]-1-(3-chlorophenyl)-pyrazole-3-carbonyl morpholine) | Example 8A 153.1 mg, 87% of theory | HPLC (1): $R_t$ = 5.03 min<br>MS (ESIpos): m/z = 468 (M + H)⁺<br>¹H-NMR(300 MHz, DMSO-$d_6$): δ = 7.74 (d, 1H), 7.68-7.41 (m, 6H), 7.28 (d, 1H), 7.08 (s, 1H), 4.02-3.92 (m, 2H), 3.73-3.57 (m, 6H). |
| 4 | (structure: 5-[3-(trifluoromethoxy)phenyl]-1-(3-chlorophenyl)-pyrazole-3-carbonyl morpholine) | Example 9A 77.6 mg, 66% of theory | LC-MS (3): $R_t$ = 2.47 min<br>MS (ESIpos): m/z = 452 (M + H)⁺<br>¹H-NMR (400 MHz, DMSO-$d_6$): δ = 7.59-7.44 (m, 4H), 7.44-7.38 (m, 2H), 7.28 (d, 1H), 7.18 (s, 1H), 7.08 (s, 1H), 3.99-3.94 (m, 2H), 3.7-3.6 (m, 6H). |
| 5 | (structure: 5-[3-(trifluoromethoxy)phenyl]-1-(3-chlorophenyl)-pyrazole-3-carbonyl 1,4-oxazepane) | Example 9A 52.8 mg, 62% of theory | LC-MS (2): $R_t$ = 2.77 min<br>MS (ESIpos): m/z = 466 (M + H)⁺<br>¹H-NMR (400 MHz, CDCl₃): δ = 7.38-7.12 (m, 6H), 7.05-6.96 (m, 2H), 6.95-6.91 (m, 1H), 4.11-4.01 (m, 2H), 3.87-3.71 (m, 6H), 2.05-1.97 (m, 2H). |

-continued

| Ex. No. | Structure | Prepared from yield | Analytical data HPLC/LC-MS (method) MS, ¹H-NMR |
|---|---|---|---|
| 6 | 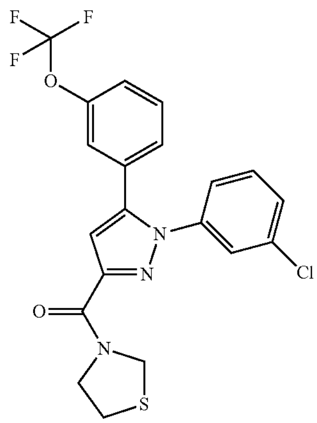 | Example 9A 45.3 mg, 55% of theory | LC-MS (3): $R_t$ = 2.98 min<br>MS (ESIpos): m/z = 454 (M + H)⁺<br>¹H-NMR (400 MHz, CDCl₃):<br>δ = 7.46-7.17 (m, 6H), 7.14-6.98 (m, 3H), 5.14 (s, 1H), 4.83 (s, 1H), 4.45-4.35 (m, 1H), 4.13 (m, 1H), 3.18-3.03 (m, 2H). |
| 7 | 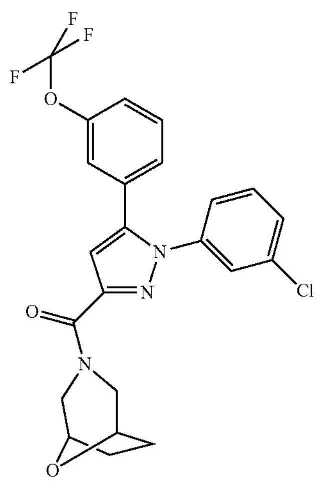 | Example 9A 51 mg, 58% of theory | LC-MS (3): $R_t$ = 2.84 min<br>MS (ESIpos): m/z = 478 (M + H)⁺<br>¹H-NMR (400 MHz, CDCl₃):<br>δ = 7.45-7.16 (m, 6H), 7.08 (s, 2H), 7.04 (s, 1H), 5.4-5.32 (m, 1H), 4.86 (m, 1H), 3.93-3.82 (m, 2H), 3.77-3.66 (m, 2H), 2.18-1.94 (m, 4H). |
| 8 | 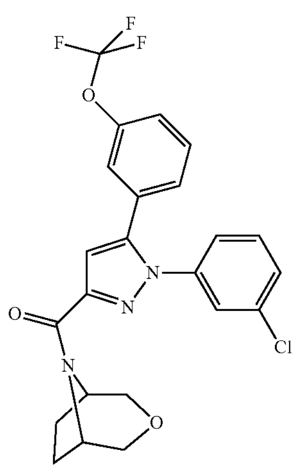 | Example 9A 53.4 mg, 61% of theory | LC-MS (2): $R_t$ = 2.87 min<br>MS (ESIpos): m/z = 478 (M + H)⁺<br>¹H-NMR (400 MHz, CDCl₃):<br>δ = 7.46-7.14 (m, 6H), 7.12-6.9 (m, 3H), 4.61 (d, 1H), 4.53-4.31 (m, 3H), 3.57 (d, 1H), 3.17 (d, 1H), 1.95 (s, 4H). |

-continued

| Ex. No. | Structure | Prepared from yield | Analytical data HPLC/LC-MS (method) MS, ¹H-NMR |
|---|---|---|---|
| 9 | (structure) | Example 9A 50.5 mg, 61% of theory | LC-MS (3): $R_t$ = 2.44 min<br>MS (ESIpos): m/z = 452 (M + H)⁺<br>¹H-NMR (400 MHz, CDCl₃):<br>δ = 7.45-77.3 (m, 3H), 7.28-7.18 (m, 3H), 7.12-7.0 (m, 3H), 4.6 (d, 1H), 4.2-4.1 (m, 2H), 3.92-3.85 (m, 1H), 3.8 (s, 1H), 2.17-1.98 (m, 2H). |
| 10 | (structure) | Example 9A 42 mg, 51% of theory | LC-MS (2): $R_t$ = 2.48 min<br>MS (ESIpos): m/z = 452 (M + H)⁺<br>Angle of rotation (methanol): α = −24.3°<br>¹H-NMR (400 MHz, CDCl₃):<br>δ = 7.43-7.3 (m, 3H), 7.3-7.2 (m, 3H), 7.15-7.0 (m, 3H), 4.62-4.55 (m, 1H), 4.32-4.1 (m, 2H), 3.92-3.78 (m, 2H), 2.18-1.98 (m, 2H). |
| 11 | (structure) | Example 9A 97.1 mg, 57% of theory | LC-MS (1): $R_t$ = 2.77 min<br>MS (ESIpos): m/z = 468 (M + H)⁺<br>¹H-NMR (400 MHz, DMSO-d₆): δ = 7.59-7.38 (m, 6H), 7.28 (d, 1H), 7.18 (s, 1H), 7.07 (s, 1H), 4.12 (s, 1H, broad), 3.92 (s, 1H, broad), 2.72-2.66 (m, 4H). |

| Ex. No. | Structure | Prepared from yield | Analytical data HPLC/LC-MS (method) MS, $^1$H-NMR |
|---|---|---|---|
| 12 | [Structure: 5-(3-trifluoromethylphenyl)-1-(3-chlorophenyl)-1H-pyrazol-3-yl carbonyl linked to 3-hydroxypyrrolidine] | Example 7A 39 mg, 47% of theory | LC-MS (2): $R_t$ = 2.42 min MS (ESIpos): m/z = 436 (M + H)$^+$ $^1$H-NMR (400 MHz, CDCl$_3$): δ = 7.65-7.0 (m, 9H), 4.65-4.55 (m, 1H), 4.32-4.1 (m, 2H), 3.9-3.75 (m, 2H), 2.15-1.95 (m, 2H). |
| 13 | [Structure: 5-(3-trifluoromethoxyphenyl)-1-(3-chlorophenyl)-1H-pyrazol-3-yl carbonyl linked to 2-(hydroxymethyl)morpholine] | Example 9A; Amine used as 2-({[tert-butyl(dimethyl)silyl]oxy}-methyl)morpholine 38.1 mg, 20% of theory | LC-MS (1): $R_t$ = 2.25 min MS (ESIpos): m/z = 482 (M − C$_6$H$_{14}$Si)− $^1$H-NMR (400 MHz, DMSO-d$_6$): δ = 7.45-7.2 (m, 7H), 7.12-6.99 (m, 2H), 4.9 (d, 0.5H), 4.75 (d, 0.5H), 4.6 (d, 0.5H), 4.44 (d, 0.5H), 4.01 (t, 1H), 3.83-3.6 (m, 4H) 3.53-3.4 (m, 1H), 3.25 (t, 0.5H), 2.92 (t, 0.5H), 2.19 (t, 0.5H), 1.93 (t, 0.5H). |

Example 14

1-{[1-(3-Chlorophenyl)-5-(3-trifluoromethoxyphenyl)-1H-pyrazol-3-yl]carbonyl}piperazine

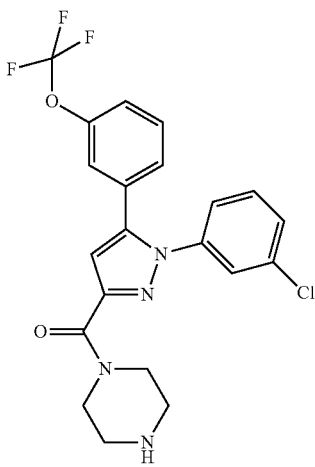

Under exclusion of oxygen, 5 ml of dichloromethane and 1 ml of trifluoroacetic acid were added to 140 mg (0.25 mmol) of tert-butyl 4-{[1-(3-chlorophenyl)-5-(3-trifluoromethoxyphenyl)-1H-pyrazol-3-yl]carbonyl}piperazine-1-carboxylate, prepared from the compound of example 9A and tert-butyl piperazine-1-carboxylate in analogy to example 1, and the mixture is stirred for 12 hours at room temperature. The reaction mixture is diluted with dichloromethane and washed with a sodium bicarbonate solution and a sodium chloride solution. The organic phase is dried over sodium sulfate and concentrated on a rotary evaporator. 101 mg (88% yield of theory) of product are obtained. By thorough drying in high vacuum at 60° C. an analytical sample is freed of solvent residues.

LC-MS (method 2): $R_t$=1.92 min

MS (ESIpos): m/z=451 (M+H)$^+$

¹H-NMR (400 MHz, DMSO-d₆): δ=7.59-7.38 (m, 6H), 7.27 (d, 1H), 7.17 (s, 1H), 7.04 (s, 1H), 3.83 (s, 2H), 3.59 (s, 2H), 279-2.69 (m, 4H).

Example 15

4-{[1-(3-Chlorophenyl)-5-(3-trifluoromethylthiophenyl)-1H-pyrazol-3-yl]carbonyl}-piperazine-1-carbaldehyde

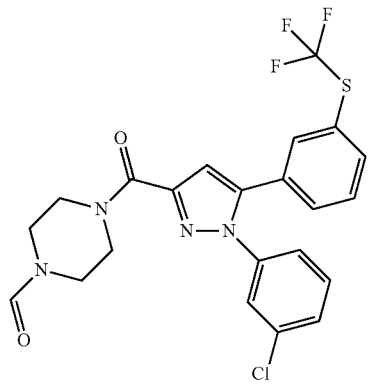

Under exclusion of oxygen, 17.2 mg (0.09 mmol) of EDC and 11.7 mg (0.09 mmol) of HOBt and 8.3 mg (0.18 mmol) of formic acid are added to a solution of 35.0 mg (0.07 mmol) of 1-{[1-(3-chlorophenyl)-5-(3-trifluoromethylthiophenyl)-1H-pyrazol-3-yl]carbonyl}piperazine, prepared from the compound of example 8A and piperazine in analogy to example 1, in 1 ml DMF, and the mixture is stirred for 72 hours at room temperature. The reaction mixture is separated by preparative HPLC. 15.7 mg (42% yield of theory) of product are obtained.

LC-MS (method 2): $R_t$=2.6 min

MS (ESIpos): m/z=495 (M+H)⁺

¹H-NMR (400 MHz, CDCl₃): δ=8.14 (s, 1H), 7.66 (d, 1H), 7.51-7.23 (m, 6H), 7.11-6.98 (m, 2H), 4.19 (d, 2H), 3.85 (d, 2H), 3.69 (s, 2H), 3.51 (s, 2H).

Example 16 and Example 17

Starting from 100 mmol of the corresponding pyrazole carboxylic acid, the compounds listed in the table are prepared in analogy to example 1 (amide coupling by means of TBTU, solvent DMF, purification of the crude product by preparative HPLC, detection of the respective molecular weight as [M+H]⁺):

| Example No. | Structure | Molecular weight | $R_t$ [min] | LC/MS method |
|---|---|---|---|---|
| 16 | 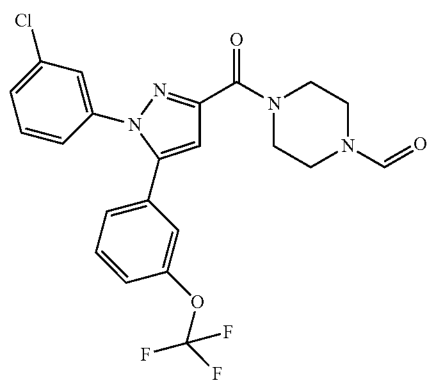 | 478.1 | 2.17 | 4 |
| 17 | 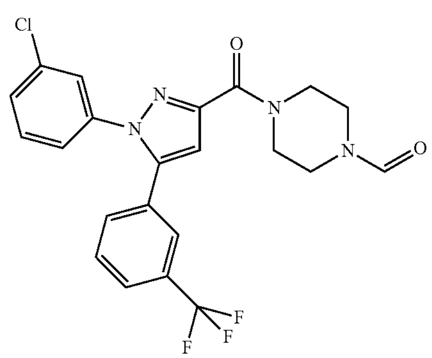 | 462.9 | 2.15 | 4 |

The following compounds are prepared in analogy to example 1:

| Ex. No. | Structure | Prepared from yield | Analytical data HPLC/LC-MS (method) MS, ¹H-NMR |
|---|---|---|---|
| 18 | (structure: 5-[3-(trifluoromethyl)phenyl]-1-(3-chlorophenyl)-pyrazole-3-carbonyl piperazine) | Example 7A 51.7 mg, 85% of theory | LC-MS (1): $R_t$ = 1.62 min<br>MS (ESIpos): m/z = 434 (M + H)$^+$<br>¹H-NMR (400 MHz, CDCl$_3$):<br>δ = 7.57 (d, 1H), 7.45 (s, 1H), 7.41 (t, 1H), 7.36-7.25 (m, 3H), 7.23-7.15 (m, 1H), 6.99 (d, 1H), 6.92 (s, 1H), 4.03 (s, 2H), 3.78 (s, 2H), 3.0-2.85 (m, 4H). |
| 19 | (structure: Boc-piperazine amide analog) | Example 7A 85 mg, 73% of theory | LC-MS (2): $R_t$ = 3.09 min<br>MS (ESIpos): m/z = 535 (M + H)$^+$<br>¹H-NMR (300 MHz, CDCl$_3$):<br>δ = 7.63 (d, 1H), 7.56-7.44 (m, 2H), 7.42-7.33 (m, 3H), 7.31-7.27 (m, 1H), 7.06 (d, 1H), 7.0 (s, 1H), 4.13-4.05 (m, 2H), 3.85-3.75 (m, 2H), 3.6-3.48 (m, 4H), 1.48 (s, 9H). |
| 20 | (structure: Boc-(methyl)piperazine amide analog) | Example 7A 165.3 mg, 74% of theory | HPLC (1): $R_t$ = 5.64 min<br>MS (ESIpos): m/z = 549 (M + H)$^+$<br>¹H-NMR (400 MHz, DMSO-d$_6$): δ = 7.76 (d, 1H), 7.67-7.56 (m, 3H), 7.52 (d, 2H), 7.46 (t, 1H), 7.27 (d, 1H), 7.11 s, 1H), 4.88-4.68 (m, 1H), 4.51-4.27 (m, 1H), 4.07-3.74 (m, 2H), 3.17-2.76 (m, 3H), 1.42 (s, 9H), 1.3-1.12 (m, 3H). |

-continued

| Ex. No. | Structure | Prepared from yield | Analytical data HPLC/LC-MS (method) MS, ¹H-NMR |
|---|---|---|---|
| 21 | 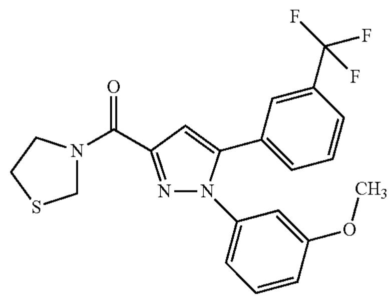 | Example 28A 57.6 mg, 69% of theory | LC-MS (2): $R_t$ = 2.91 min MS (ESIpos): m/z = 434 (M + H)⁺ ¹H-NMR (400 MHz, DMSO-d₆): δ = 7.74 (d, 1H), 7.65-7.57 (m, 3H), 7.36 (t, 1H), 7.21 (s, 1H), 7.06-6.95 (m, 2H), 6.89 (d, 1H), 5.05 (s, 1H), 4.7 (s, 1H), 4.27-4.21 (m, 1H), 3.91-3.84 (m, 1H), 3.7 (s, 3H), 3.15-3.03 (m, 2H). |
| 22 | 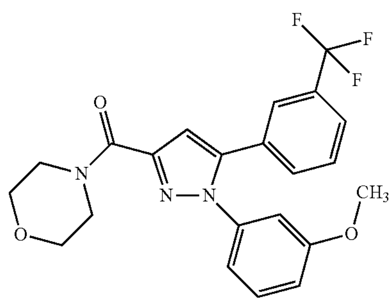 | Example 28A 63.8 mg, 77% of theory | LC-MS (1): $R_t$ = 2.3 min MS (ESIpos): m/z = 432 (M + H)⁺ ¹H-NMR(400 MHz, DMSO-d₆): δ = 7.74 (d, 1H), 7.65-7.56 (m, 3H), 7.35 (t, 1H), 7.11 (s, 1H), 7.02 (d, 1H), 6.94 (s, 1H), 6.86 (d, 1H), 3.99 (s, 2H), 3.73-3.58 (m, 9H). |
| 23 | 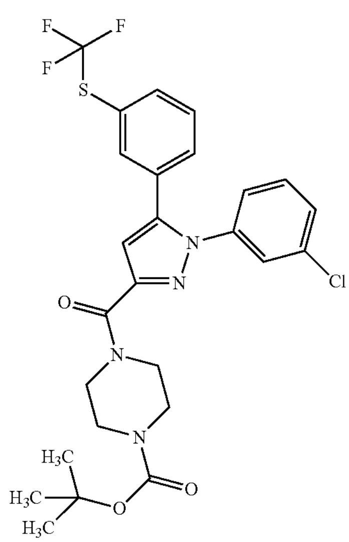 | Example 8A 154.5 mg, 68% of theory | LC-MS (2): $R_t$ = 3.21 min MS (ESIpos): m/z = 567 (M + H)⁺ ¹H-NMR (300 MHz, CDCl₃): δ = 7.65 (d, 1H), 7.5-7.38 (m, 3H), 7.38-7.3 (m, 3H), 7.06 (d, 1H), 6.98 (s, 1H), 4.15-4.05 (m, 2H), 3.85-3.74 (m, 2H), 3.6-3.47 (m, 4H), 1.48 (s, 9H). |

| Ex. No. | Structure | Prepared from yield | Analytical data HPLC/LC-MS (method) MS, $^1$H-NMR |
|---|---|---|---|
| 24 | 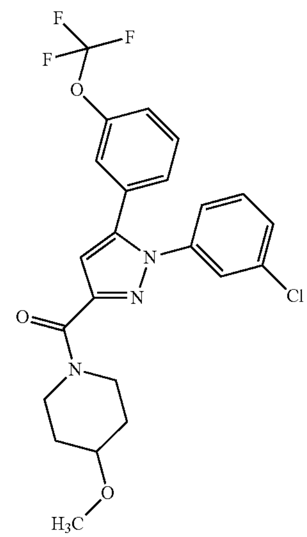 | Example 9A 46.7 mg, 53% of theory | LC-MS (1): $R_t$ = 2.65 min MS (ESIpos): m/z = 480 (M + H)$^+$ $^1$H-NMR (400 MHz, DMSO-d$_6$): δ = 7.44-7.16 (m, 6H), 7.12-7.0 (m, 2H), 6.93 (s, 1H), 4.37-4.22 (m, 1H), 4.18-4.02 (m, 1H), 3.84-3.68 (m, 1H), 3.63-3.46 (m, 2H), 3.39 (s, 3H), 2.04-1.87 (m, 2H), 1.78-1.56 (m, 2H). |
| 25 | 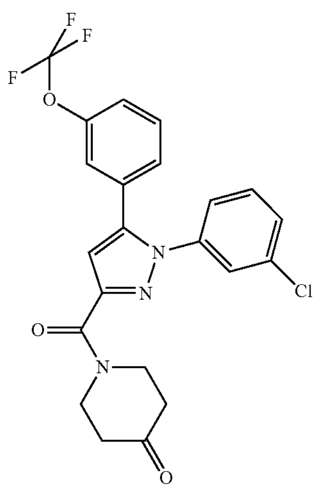 | Example 9A 69.9 mg, 38% of theory | LC-MS (3): $R_t$ = 2.65 min MS (ESIpos): m/z = 464 (M + H)$^+$ $^1$H-NMR (400 MHz, CDCl$_3$): δ = 7.45-7.34 (m, 3H), 7.32-7.2 (m, 3H), 7.09 (d, 1H), 7.04 (s, 2H), 4.45-4.35 (m, 2H), 4.12-4.03 (m, 2H), 2.66-2.56 (m, 4H). |
| 26 | 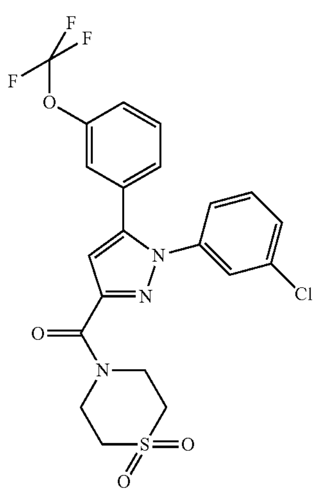 | Example 9A 50.9 mg, 56% of theory | LC-MS (2): $R_t$ = 2.69 min MS (ESIpos): m/z = 500 (M + H)$^+$ $^1$H-NMR (400 MHz, CDCl$_3$): δ = 7.45-7.36 (m, 2H), 7.36-7.17 (m, 4H), 7.12-7.0 (m, 3H), 4.65 (s, 2H), 4.29 (s, 2H), 3.2 (d, 4H). |

| Ex. No. | Structure | Prepared from yield | Analytical data HPLC/LC-MS (method) MS, ¹H-NMR |
|---|---|---|---|
| 27 | 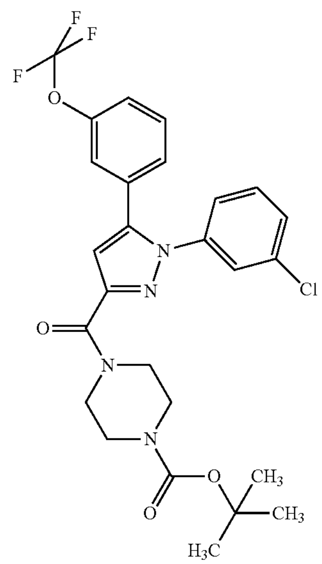 | Example 9A 150 mg, 50% of theory | LC-MS (2): $R_t$ = 3.15 min MS (ESIpos): m/z = 551 (M + H)⁺ ¹H-NMR (400 MHz, DMSO-d₆): δ = 7.59-7.44 (m, 4H), 7.41 (d, 2H), 7.29 (d, 1H), 7.18 (s, 1H), 7.09 (s, 1H), 3.93 (s, 2H, broad), 3.64 (s, 2H, broad), 3.41 (s, 4H, broad), 1.42 (s, 9H). |
| 28 | 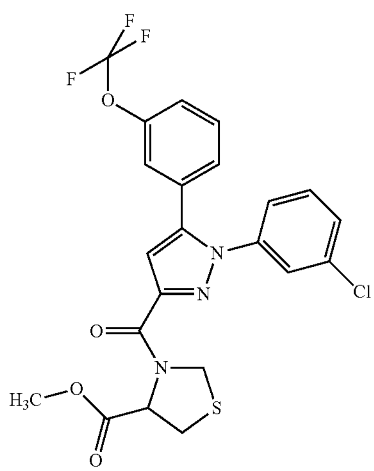 | Example 9A 32 mg, 14% of theory | LC-MS (2): $R_t$ = 3.03 min MS (ESIpos): m/z = 512 (M + H)⁺ ¹H-NMR (400 MHz, DMSO-d₆): δ = 7.6-7.4 (m, 6H), 7.22-7.12 (m, 3H), 5.8, 5.4, 5.1 (d, d, t, 2H, various signals through E/Z isomers), 5.0, 4.9, 4.67 (3d, 2H, various signals through E/Z isomers), 3.7, 3.6 (2s, 3H, various signals through E/Z isomers), 3.58-3.4 (m, 1H). |
| 29 | 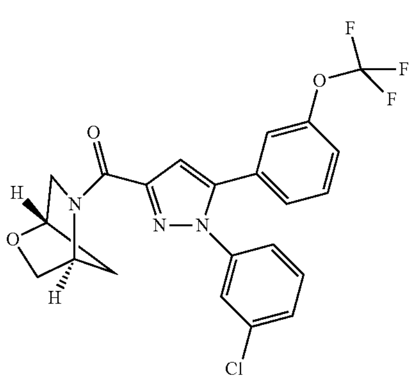 | Example 9A 41 mg, 48% of theory | LC-MS (2): $R_t$ = 2.71 min MS (ESIpos): m/z = 464 (M + H)⁺ ¹H-NMR (400 MHz, DMSO-d₆): δ = 7.6-7.4 (m, 6H), 7.35-7.25 (m, 1H), 7.2-7.11 (m, 2H), 5.6, 4.95 (2s, 1H, various signals through E/Z isomers), 4.66 (s, 1H), 3.9-3.7 (m, 3H), 3.5, 3.4 (2d, 1H, various signals through E/Z isomers), 1.95-1.8 (m, 2H). |

| Ex. No. | Structure | Prepared from yield | Analytical data HPLC/LC-MS (method) MS, ¹H-NMR |
|---|---|---|---|
| 30 | 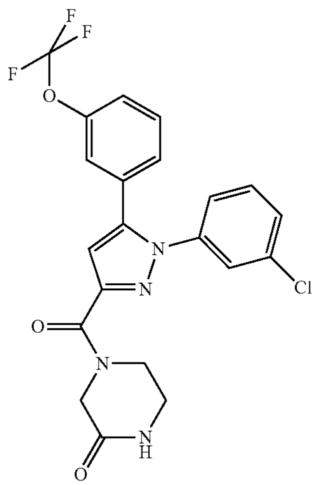 | Example 9A 43.4 mg, 51% of theory | LC-MS (2): $R_t$ = 2.40 min MS (ESIpos): m/z = 465 (M + H)⁺ |
| 31 | 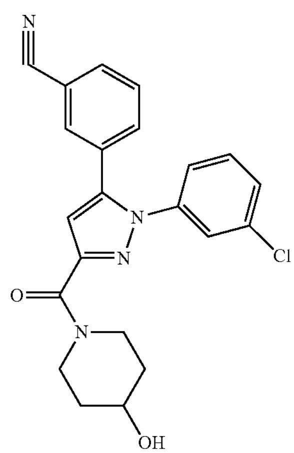 | Example 23A 24.7 mg, 30% of theory | LC-MS (3): $R_t$ = 2.06 min MS (ESIpos): m/z = 407 (M + H)⁺ ¹H-NMR (400 MHz, CDCl₃): δ = 7.66 (s, 1H), 7.59-7.43 (m, 3H), 7.36 (s, 2H), 7.32-7.23 (m, 1H), 7.05 (d, 1H), 6.95 (s, 1H), 4.5-4.37 (m, 1H), 4.32-4.21 (m, 1H), 4.08-3.97 (m, 1H), 3.73-3.61 (m, 1H), 3.48-3.36 (m, 1H), 2.08-1.94 (m, 2H), 1.71-1.58 (m, 2H). |
| 32 | 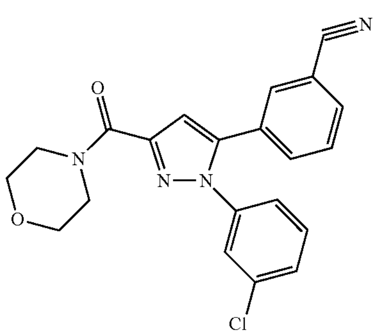 | Example 23A 64.1 mg, 53% of theory | HPLC (2): $R_t$ = 4.39 min MS (ESIpos): m/z = 393 (M + H)⁺ ¹H-NMR (300 MHz, DMSO-d₆): δ = 7.92-7.84 (m, 2H), 7.63-7.42 (m, 5H), 7.24 (d, 1H), 7.12 (s, 1H), 3.97 (s, 2H), 3.75-3.57 (m, 6H). |
| 33 | 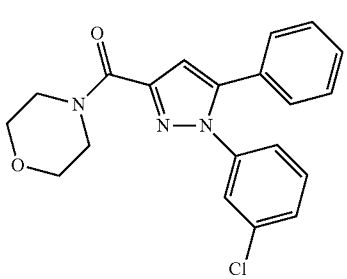 | Example 24A 43.2 mg, 70% of theory | HPLC (2): $R_t$ = 5.05 min MS (ESIpos): m/z = 368 (M + H)⁺ ¹H-NMR (400 MHz, DMSO-d₆): δ = 7.53-7.35 (m, 6H), 7.33-7.16 (m, 3H), 6.95 (s, 1H), 3.98 (s, 2H), 3.72-3.57 (m, 6H). |

-continued

| Ex. No. | Structure | Prepared from yield | Analytical data HPLC/LC-MS (method) MS, ¹H-NMR |
|---|---|---|---|
| 34 | 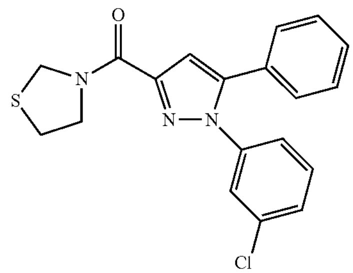 | Example 24A 49.1 mg, 79% of theory | HPLC (2): $R_t$ = 5.11 min MS (ESIpos): m/z = 370 (M + H)⁺ ¹H-NMR (400 MHz, DMSO-$d_6$): δ = 7.55-7.37 (m, 6H), 7.32-7.23 (m, 3H), 7.05 (s, 1H), 5.06 (s, 1H), 4.69 (s, 1H), 4.27-4.2 (m, 1H), 3.9-3.83 (m, 1H), 3.16-3.03 (m, 2H). |
| 35 | 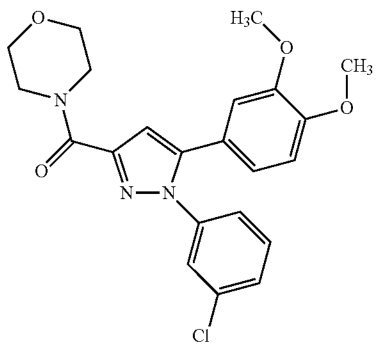 | Example 25A 52.9 mg, 89% of theory | HPLC (2): $R_t$ = 4.32 min MS (ESIpos): m/z = 428 (M + H)⁺ ¹H-NMR (400 MHz, DMSO-$d_6$): δ = 7.52-7.43 (m, 3H), 7.26 (d, 1H), 6.98-6.91 (m, 2H), 6.86-6.83 (m, 1H), 6.78 (dd, 1H), 4.01-3.95 (m, 2H), 3.75 (s, 3H), 3.69-3.58 (m, 9H). |
| 36 | 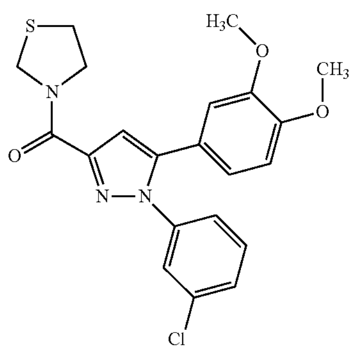 | Example 25A 47.6 mg, 79% of theory | HPLC (2): $R_t$ = 4.68 min MS (ESIpos): m/z = 430 (M + H)⁺ ¹H-NMR (400 MHz, DMSO-$d_6$): δ = 7.59-7.44 (m, 3H), 7.28 (d, 1H), 7.03 (s, 1H), 6.96 (d, 1H), 6.87-6.84 (m, 1H), 6.81-6.75 (m, 1H), 5.05 (s, 1H), 4.69 (s, 1H), 4.23 (t, 1H), 3.86 (t, 1H), 3.75 (s, 3H), 3.62 (s, 3H). |
| 37 | 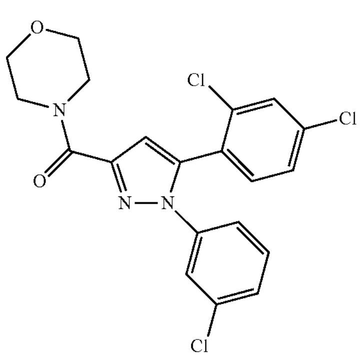 | Example 26A 38.3 mg, 69% of theory | HPLC (2): $R_t$ = 4.98 min MS (ESIpos): m/z = 436 (M + H)⁺ ¹H-NMR (400 MHz, DMSO-$d_6$): δ = 7.75 (s, 1H), 7.62-7.53 (m, 2H), 7.48-7.37 (m, 3H), 7.14 (d, 1H), 6.96 (s, 1H), 4.04-3.93 (m, 2H), 3.66 (s, 6H). |

| Ex. No. | Structure | Prepared from yield | Analytical data HPLC/LC-MS (method) MS, $^1$H-NMR |
|---|---|---|---|
| 38 | 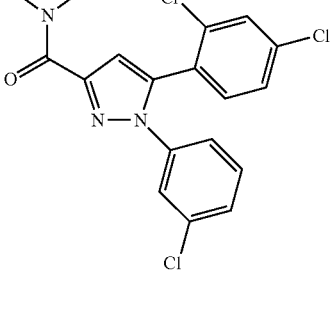 | Example 26A 27.8 mg, 50% of theory | HPLC (2): $R_t$ = 5.34 min MS (ESIpos): m/z = 438 (M + H)$^+$ $^1$H-NMR (400 MHz, DMSO-d$_6$): δ = 7.75 (s, 1H), 7.63-7.53 (m, 2H), 7.51-7.35 (m, 3H), 7.17 (d, 1H), 7.04 (s, 1H), 5.07 (s, 1H), 4.69 (s, 1H), 4.3-4.19 (m, 1H), 3.92-3.83 (m, 1H), 3.19-3.03 (m, 2H). |
| 39 | 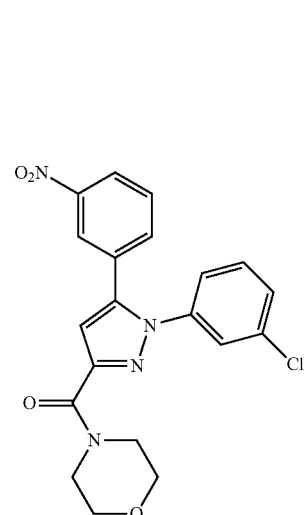 | Example 27A 48.9 mg, 81% of theory | HPLC (2): $R_t$ = 4.45 min MS (ESIpos): m/z = 413 (M + H)$^+$ $^1$H-NMR (400 MHz, DMSO-d$_6$): δ = 8.27-8.21 (m, 1H), 8.13 (s, 1H), 7.73-7.65 (m, 2H), 7.59 (s, 1H), 7.54 (d, 1H), 7.4 (t, 1H), 7.29 (t, 1H), 7.18 (s, 1H), 3.97 (s, 2H), 3.72-3.59 (m, 6H). |
| 40 | 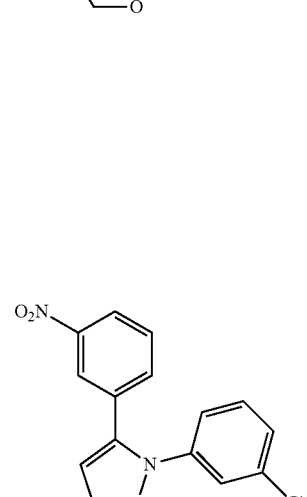 | Example 27A 49.2 mg, 82% of theory | HPLC (2): $R_t$ = 4.78 min MS (ESIpos): m/z = 415 (M + H)$^+$ $^1$H-NMR (400 MHz, DMSO-d$_6$): δ = 8.24 (d, 1H), 8.14 (s, 1H), 7.74-7.6 (m, 3H), 7.55 (d, 1H), 7.47 (t, 1H), 7.31 (d, 1H), 7.27 (s, 1H), 5.05 (s, 1H), 4.7 (s, 1H), 4.24 (t, 1H), 3.88 (t, 1H), 3.16-3.04 (m, 2H). |

The following compounds are prepared in analogy to example 14:

| Ex. No. | Structure | Prepared from yield | Analytical data HPLC/LC-MS (method) MS, ¹H-NMR |
|---|---|---|---|
| 41 | (piperazine with CH₃ substituent, N-acyl linked to pyrazole bearing 3-(trifluoromethyl)phenyl and N-(3-chlorophenyl)) | Example 20 43 mg, 42% of theory | HPLC (2): $R_t$ = 4.45 min MS (ESIpos): m/z = 449 (M + H)⁺ ¹H-NMR (400 MHz, DMSO-$d_6$): δ = 7.76 (d, 1H), 7.68-7.41 (m, 6H), 7.26 (d, 1H), 7.07 (s, 1H), 4.68-4.55 (m, 1H), 4.27 (d, 1H), 3.09-2.64 (m, 5H), 1.30 (s, 3H). |

The following compounds are prepared in analogy to example 15:

| Ex. No. | Structure | Prepared from yield | Analytical data HPLC/LC-MS (method) MS |
|---|---|---|---|
| 42 | (N-formyl piperazine with CH₃ substituent linked to pyrazole bearing 3-(trifluoromethyl)phenyl and N-(3-chlorophenyl)) | Example 41 21.4 mg, 71% of theory | HPLC (2): $R_t$ = 4.69 min MS (ESIpos): m/z = 477 (M + H)⁺ |

The following compounds are prepared in analogy to example 16:

| Example No. | Structure | Molecular weight | R$_t$ [min] | LC/MS method |
|---|---|---|---|---|
| 43 | 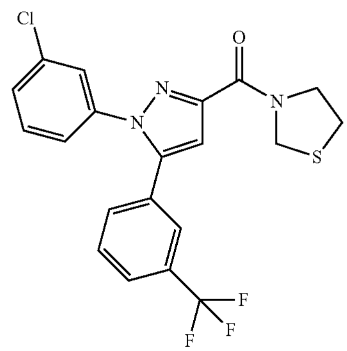 | 437.9 | 2.54 | 4 |
| 44 | 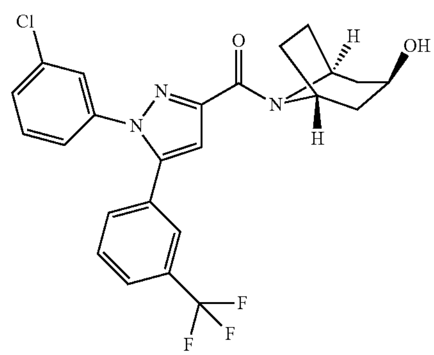 | 475.9 | 2.38 | 4 |
| 45 | 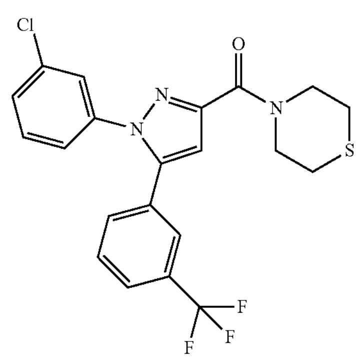 | 451.9 | 2.52 | 4 |
| 46 | 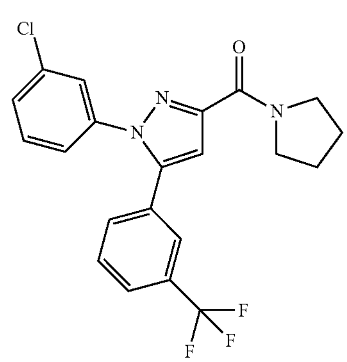 | 419.8 | 2.48 | 4 |

| Example No. | Structure | Molecular weight | $R_t$ [min] | LC/MS method |
|---|---|---|---|---|
| 47 | 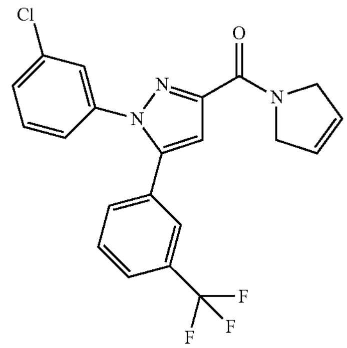 | 417.8 | 2.52 | 4 |

Example 48

4-({1-(3-Chlorophenyl)-5-[3-(trifluoromethoxy)phenyl]-1H-pyrazol-3-yl}carbonyl)-thiomorpholine-1-oxide

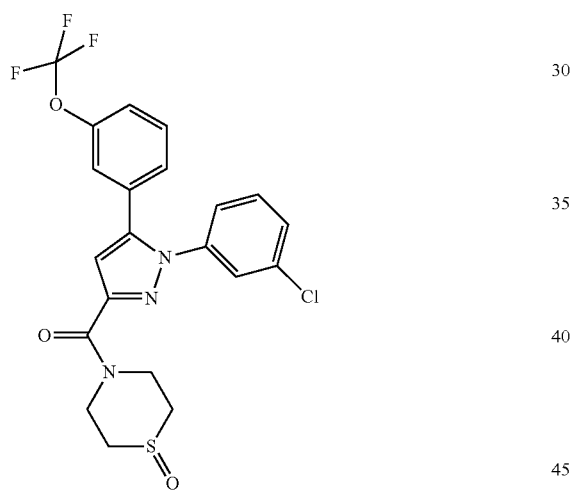

57 mg (0.23 mmol) of 70% 3-chlorperbenzoic acid are added, at 0° C., to 90 mg (0.19 mmol) of the compound of example 11 in 4 ml of dichloromethane. After stirring for 2 h at this temperature, the mixture is washed successively with a diluted sodium hydroxide solution and a thiosulfate solution and filtered through silica gel (Extrelut). The oil remaining after concentrating the eluate is purified by preparative HPLC (RP18, acetonitrile/water gradient). 20 mg (22% of theory) of the product are obtained.

LC-MS (2): $R_t$=2.5 min

MS (ESIpos): m/z=484 (M+H)$^+$ $^1$H-NMR (400 MHz, DMSO-d$_6$): δ=7.6-7.45 (m, 4H), 7.42 (d, 2H), 7.29 (d, 1H), 7.18 (s, 1H), 7.1 (s, 1H), 4.6 (d, 1H), 4.39 (d, 1H), 4.07 (t, 1H), 3.73 (t, 1H), 3.06-2.91 (m, 2H), 2.87-2.78 (m, 2H).

The following can be obtained in the same way as example 48:

| Ex. No. | Structure | Prepared from yield | Analytical data HPLC/LC-MS (method) MS, $^1$H-NMR |
|---|---|---|---|
| 49 | 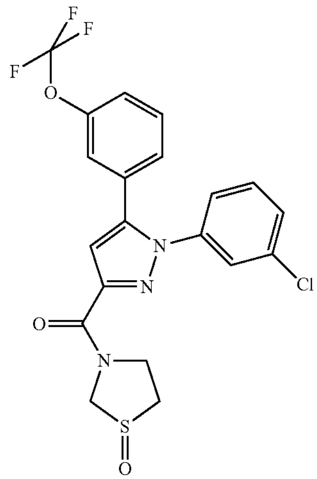 | Example 6 41 mg, 44% of theory | LC-MS (2): $R_t$ = 2.5 min MS (ESIpos): m/z = 470 (M + H)$^+$ $^1$H-NMR (400 MHz, DMSO-d$_6$): δ = 7.63-7.4 (m, 6H), 7.32 (d, 1H), 7.26-7.18 (m, 2H), 5.48, 4.98 (2d, 1H, various signals through E/Z isomers), 4.7-4.0 (m, 3H), 3.25-3.0 (m, 2H). |

B) Assessment of Physiological Activity

Abbreviations:
RPMI 1640 medium from Gibco, Invitrogen Corporation, Karlsruhe, Germany
FCS fetal calf serum The suitability of the compounds of the invention for the treatment of diseases caused by retroviruses can be shown in the following assay system:

In Vitro Assay
HIV Infection in Cell Culture

The HIV test is conducted according to the method of Pauswels et al. [cf. *Journal of Virological Methods* 1988, 20, 309-321], with modifications.

Primary human blood lymphocytes (PBLs) are enriched using Ficoll-Hypaque and stimulated, in RPMI 1640 medium, 20% fetal calf serum, with phytohemagglutinin (90 μg/ml) and interleukin-2 (40 U/ml). For the infection with the infectious HIV, the PBLs are pelletted and the cell pellet is subsequently suspended in 1 ml of a suitable diluted HIV virus adsorption solution and incubated for 1 hour at 37° C. (pellet infection). Unabsorbed virus is subsequently removed by centrifugation, and the infected cells are transferred to test plates (e.g. 96-well microtiter plates), which contain the test substances in a suitable dilution.

Alternatively, for example HIV-susceptible, permanent H9 cells (ATCC or NIAID, USA) are used instead of normal human blood lymphocytes for testing the antiviral effects of the compounds of the invention. Infected H9 cells are grown for test purposes in RPMI 1640 medium, 2% and/or 20% fetal calf serum.

The virus adsorption solution is centrifuged and the infected cell pellet is taken up in growth medium, so as to give 1×10$^5$ cells per ml. The cells infected in this way are pipetted at approx. 1×10$^4$ cells/well into the wells of 96-well microtiter plates (pellet infection). Alternatively the HIV is pipetted in separately only after preparation of the substance dilutions in the microtiter plates and after addition of the cells (supernatant infection).

The first vertical row of the microtiter plate contains only growth medium and cells that are not infected, but are otherwise treated exactly as described above (cell control). The second vertical row of the microtiter plate receives only HIV-infected cells (virus control) in growth medium. The other wells contain the compounds of the invention in various concentrations, starting from the wells of the 3rd vertical row of the microtiter plate, from which the test substances are diluted $2^{10}$-fold in 2-fold steps.

Alternatively, supernatant infections are carried out (see above), in which the cells are sown in 96-well plates. The HIV virus is then added in a volume of 50 μl.

The test preparations are incubated at 37° C., until the formation of syncytia that is typical of HIV occurs in the untreated virus control (between day 3 and 6 after infection), which is then evaluated either microscopically or by p24 ELISA detection methods (Vironostika, BioMerieux, The Netherlands) or photometrically or fluorometrically using Alamar Blue indicator dye. In the untreated virus control these test conditions result in about 20-100 syncytia, whereas the untreated cell control does not have any syncytia. Correspondingly, the ELISA test shows values smaller than 0.1 for the cell controls and values between 0.1 and 2.9 for the virus controls. Photometric evaluation of the cells treated with Alamar Blue shows extinctions smaller than 0.1 for the cell controls, whereas the virus controls have values between 0.1 and 3 at corresponding wavelengths.

The IC$_{50}$ values are determined as the concentration of the test substance at which 50% (approx. 20-100 syncytia) of the virus-induced syncytia are suppressed by the treatment with the compound of the invention. The cut-off values are set correspondingly in the ELISA test and in the photometric or fluorometric determination using Alamar Blue. In addition to determination of the antiviral effects, the treated cell cultures are also investigated microscopically with respect to cytotoxic, cytostatic or cytological changes and with respect to solubility. Active compounds that show cell-altering, cytotoxic findings in the concentration range of the activity are not assessed for their antiviral activity.

It is found that the compounds of the invention protect HIV-infected cells against virus-induced cell disruption. Experimental data is presented in Table A.

TABLE A

| Example No. | IC$_{50}$ (μM), H9 cells, 2% FCS |
|---|---|
| 2 | 0.05 |
| 4 | 0.05 |
| 5 | 0.04 |
| 6 | 0.1 |
| 10 | 0.05 |
| 15 | 0.15 |
| 32 | 0.04 |
| 33 | 0.05 |
| 34 | 0.08 |
| 35 | 0.1 |
| 43 | 0.1 |

C) Exemplary Embodiments of Pharmaceutical Compositions

The compounds of the invention can be converted into pharmaceutical preparations in the following ways:

Tablet:

Composition:

100 mg of the compound of example 1, 50 mg of lactose (monohydrate), 50 mg maize starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm

Production:

The mixture of compound of the invention, lactose and starch is granulated with a 5% solution (w/w) of the PVP in water. After drying, the granules are mixed with the magnesium stearate for 5 minutes. This mixture is compressed using a conventional tablet press (format of the tablet see above). A guideline compressive force for their compression is 15 kN.

Solution which can be Administered Orally:

Composition 500 mg of the compound of example 1, 2.5 g of polysorbate and 97 g of polyethylene glycol 400.20 g of oral solution correspond to a single dose of 100 mg of the compound of the invention.

Production

The compound of the invention is suspended in the mixture of polyethylene glycol and polysorbate with stirring. The stirring process is continued until the compound of the invention has completely dissolved.

i.v. Solution:

The compound of the invention is dissolved, in a concentration below the saturation solubility, in a physiologically acceptable solvent (e.g. isotonic saline solution, 5% glucose solution, 30% PEG 400 solution). The solution is sterilized by filtration and dispensed into sterile and pyrogen-free injection containers.

What is claimed is:

1. A method for treating retroviral diseases in humans and animals by administering a compound of formula

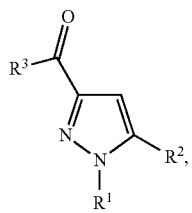

(I)

in which
R$^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, (C$_1$-C$_4$)-alkyl and (C$_1$-C$_4$)-alkoxy,
R$^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, C$_1$-C$_4$ alkyl and C$_1$-C$_4$ alkoxy,
R$^3$ represents a 5- to 8-membered heterocycle bonded via nitrogen,
whereby the heterocycle may be substituted with 1 to 3 substituents, whereby the substituents are selected independently of one another from the group consisting of halogen, hydroxy, hydroxymethyl, formyl, amino, oxo, trifluoromethyl, trifluoromethoxy, (C$_1$-C$_4$)-alkyl, (C$_1$-C$_4$)-alkoxy and (C$_1$-C$_4$)-alkoxycarbonyl,
or one of its salts, to a human or animal in need thereof.

2. The method of claim 1, wherein in the compound of formula (I)
R$^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, (C$_1$-C$_4$)-alkyl and (C$_1$-C$_4$)-alkoxy,
R$^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, (C$_1$-C$_4$)-alkyl and (C$_1$-C$_4$)-alkoxy,
R$^3$ represents pyrrolidin-1-yl, morpholin-4-yl, thiomorpholin-4-yl, 1,3-thiazolidin-3-yl, piperidin-1-yl, piperazin-1-yl or 1,4-oxazepan-4-yl,
whereby pyrrolidin-1-yl, morpholin-4-yl, thiomorpholin-4-yl, 1,3-thiazolidin-3-yl, piperidin-1-yl, piperazin-1-yl or 1,4-oxazepan-4-yl may be substituted with 1 to 3 substituents, whereby the substituents are selected independently of one another from the group consisting of hydroxy, hydroxymethyl, formyl, amino, oxo, (C$_1$-C$_4$)-alkyl, (C$_1$-C$_4$)-alkoxy and (C$_1$-C$_4$)-alkoxycarbonyl.

3. The method of claim 1, wherein in the compound of formula (I)
(a) R$^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, and $R^3$ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, or (b) $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of trifluoromethoxy and trifluoromethylthio, and $R^3$ represents an unsubstituted 5- to 8-membered heterocycle bonded via nitrogen.

4. A compound of formula

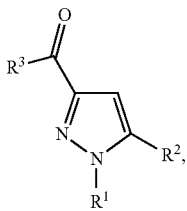

(I)

in which (a) $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, and $R^3$ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, or one of its salts;

or a compound of formula (I) in which (b) $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of trifluoromethoxy and trifluoromethylthio, and $R^3$ represents an unsubstituted 5- to 8-membered heterocycle bonded via nitrogen, or one of its salts.

5. A method for preparing (a) a compound of formula

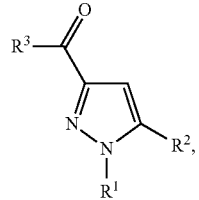

(I)

in which $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, and $R^3$ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl, or one of its salts; or (b) a compound of formula (I) in which $R^1$ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy, $R^2$ represents phenyl,
whereby phenyl may be substituted with 1 to 3 substituents, whereby the substituents are selected independently of one another from the group consisting of trifluoromethoxy and trifluoromethylthio, and R³ represents an unsubstituted 5- to 8-membered heterocycle bonded via nitrogen,
or one of its salts;
comprising reacting a compound of formula

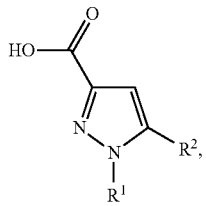
(II)

in which
R¹ and R² have the meaning indicated in (a) or (b),
with a compound of formula

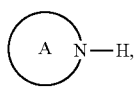
(III)

in which
A is a heterocycle as defined for R³ in (a) or (b).

6. A method for the manufacture of a medicament for the treatment of diseases, comprising mixing a compound of claim 4 with at least one inert non-toxic pharmaceutically acceptable excipient.

7. A method for the manufacture of a medicament for the treatment of retroviral diseases, comprising mixing a compound of claim 4 with at least one inert non-toxic pharmaceutically acceptable excipient.

8. A medicament containing a compound as defined in claim 4 in combination with another active substance.

9. A medicament containing at least one compound of claim 4 in combination with at least one inert, nontoxic, pharmaceutically suitable excipient.

10. A method for controlling retroviral diseases in humans and animals by administering an antivirally effective amount of (a) at least one compound of formula

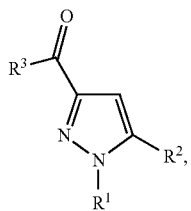
(I)

in which
R¹ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy,
R² represents phenyl,
whereby phenyl may be substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy,
and
R³ represents a 5- to 8-membered heterocycle bonded via nitrogen,
whereby the heterocycle is substituted with 1 to 3 substituents, whereby the substituents are selected independently of one another from the group consisting of halogen, hydroxy, hydroxymethyl, formyl, amino, oxo, trifluoromethyl, trifluoromethoxy, $(C_1-C_4)$-alkyl, $(C_1-C_4)$-alkoxy and $(C_1-C_4)$-alkoxycarbonyl,
(b) at least one compound of formula (I) in which
R¹ represents phenyl,
whereby phenyl is substituted with 1 to 3 substituents, whereby the substituents are selected independently of one another from the group consisting of halogen, cyano, nitro, trifluoromethyl, trifluoromethoxy, trifluoromethylthio, $(C_1-C_4)$-alkyl and $(C_1-C_4)$-alkoxy,
R² represents phenyl,
whereby phenyl may be substituted with 1 to 3 substituents, whereby the substituents are selected independently of one another from the group consisting of trifluoromethoxy and trifluoromethylthio,
and
R³ represents an unsubstituted 5- to 8-membered heterocycle bonded via nitrogen,
or one of its salts;
(c) a medicament comprising a compound of Formula (I), or one of its salts, as defined in (a) or (b), in combination with another active substance; or
(d) a medicament comprising at least one compound of Formula (I), or one of its salts, as defined in (a) or (b), in combination with at least one inert, nontoxic, pharmaceutically suitable excipient;
to a human or animal in need thereof.

11. The method of claim 10, wherein the retroviral disease is an infection with the HI-virus.

\* \* \* \* \*